(12) United States Patent
Schlenoff

(10) Patent No.: US 7,629,133 B2
(45) Date of Patent: *Dec. 8, 2009

(54) CONTROLLED TRANSPORT THROUGH MULTIPLE REVERSIBLE INTERACTION POINT MEMBRANES

(75) Inventor: Joseph B. Schlenoff, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 287 days.

This patent is subject to a terminal disclaimer.

(21) Appl. No.: 11/764,350

(22) Filed: Jun. 18, 2007

(65) Prior Publication Data

US 2007/0259452 A1    Nov. 8, 2007

Related U.S. Application Data

(63) Continuation of application No. 11/085,926, filed on Mar. 22, 2005, now Pat. No. 7,238,536.

(60) Provisional application No. 60/555,394, filed on Mar. 22, 2004.

(51) Int. Cl.
  *G01N 21/76* (2006.01)
  *G01N 33/53* (2006.01)
  *G01N 33/544* (2006.01)
  *G01N 33/545* (2006.01)
  *C12Q 1/68* (2006.01)

(52) U.S. Cl. ............................. 435/7.1; 435/6; 436/528; 436/531; 436/164; 436/172; 422/52; 422/82.01; 422/82.02

(58) Field of Classification Search .................. None
  See application file for complete search history.

(56) References Cited

U.S. PATENT DOCUMENTS

| 3,467,604 A | 9/1969 | Michaels |
| 4,168,112 A | 9/1979 | Ellis et al. |
| 4,169,023 A | 9/1979 | Sata et al. |
| 4,501,835 A | 2/1985 | Berke |
| 4,654,235 A | 3/1987 | Effenberger et al. |
| 4,673,566 A | 6/1987 | Goosen et al. |
| 4,895,809 A | 1/1990 | Schlabach et al. |
| 5,061,445 A | 10/1991 | Zoski et al. |
| 5,068,088 A | 11/1991 | Hall et al. |
| 5,075,172 A | 12/1991 | Dixon et al. |
| 5,093,268 A | 3/1992 | Leventis et al. |

(Continued)

OTHER PUBLICATIONS

Barker, S.L.R., et al., "Control of Flow Direction in Microfluidic Devices with Polyelectrolyte Multilayers," *Analytical Chemistry*, Dec. 15, 2000, pp. 5925-5929, vol. 72, No. 24.

(Continued)

*Primary Examiner*—Unsu Jung
(74) *Attorney, Agent, or Firm*—Senniger Powers LLP

(57) ABSTRACT

A method for causing a membrane to become permeable to a first chemical species, in which the membrane is contacted with a solution comprising a second chemical species. The membrane comprises a polyelectrolyte complex film comprising a positively-charged polyelectrolyte and a negatively-charged polyelectrolyte. The second chemical species selectively interacts with the membrane, and selective interaction of the second chemical species with the membrane causes the membrane to become permeable to the first chemical species, thereby causing the first chemical species to permeate the membrane.

16 Claims, 11 Drawing Sheets

U.S. PATENT DOCUMENTS

| | | | |
|---|---|---|---|
| 5,147,806 A | 9/1992 | Kamin et al. |
| 5,208,111 A | 5/1993 | Decher et al. |
| 5,221,605 A | 6/1993 | Bard et al. |
| 5,238,808 A | 8/1993 | Bard et al. |
| 5,247,243 A | 9/1993 | Hall et al. |
| 5,296,191 A | 3/1994 | Hall et al. |
| 5,310,687 A | 5/1994 | Bard et al. |
| 5,324,457 A | 6/1994 | Zhang et al. |
| 5,711,915 A | 1/1998 | Siegmund et al. |
| 5,807,636 A | 9/1998 | Sheu et al. |
| 6,136,268 A | 10/2000 | Ala-Kleme et al. |
| 6,402,918 B1 | 6/2002 | Schlenoff et al. |
| 6,451,871 B1 | 9/2002 | Winterton et al. |
| 6,468,657 B1 | 10/2002 | Hou et al. |
| 6,610,789 B2 | 8/2003 | Watakabe et al. |
| 6,660,367 B1 | 12/2003 | Yang et al. |
| 6,682,638 B1 | 1/2004 | Prohaska et al. |
| 6,841,054 B2 | 1/2005 | Schlenoff et al. |
| 6,860,980 B2 | 3/2005 | Locascio et al. |
| 7,101,575 B2 | 9/2006 | Donath et al. |
| 7,101,947 B2 | 9/2006 | Schlenoff et al. |
| 7,223,327 B2 | 5/2007 | Schlenoff et al. |
| 2004/0022691 A1 | 2/2004 | Allen et al. |
| 2004/0060481 A1 | 4/2004 | Schlenoff |
| 2004/0084312 A1 | 5/2004 | Warner et al. |
| 2004/0265603 A1 | 12/2004 | Schlenoff |
| 2005/0025675 A1 | 2/2005 | Schlenoff et al. |

OTHER PUBLICATIONS

Berg, M.C., et al., "Controlling Mammalian Cell Interactions on Patterned Polyelectrolyte Multilayer Surfaces," *Langmuir*, 2004, pp. 1362-1368, vol. 20, No. 4.

Boura, C., et al., "Endothelial Cells Grown on Thin Polyelectrolyte Multilayered Films: An Evaluation of a New Versatile Surface Modification," *Biomaterials 24*, 2003, pp. 3521-3530.

Caruso, F., et al., "Assembly of Alternating Polyelectrolyte and Protein Multilayer Films for Immunosensing," *Langmuir*, 1997, pp. 3427-3433, vol. 13, No. 13.

Cheng, Y., et al., "Ultrathin Potypeptide Multilayer Films for the Fabrication of Model Liquid/Liquid Electrochemical Interfaces," J. Phys. Chem. B 1999, pp. 8726-8731, vol. 103, No. 41, Published Sep. 18, 1999.

Chen, W., et al., "Layer-by-Layer Deposition: A Tool for Polymer Surface Modification," *Macromolecules*, 1997, pp. 78-86, vol. 30, No. 1.

Chluba, J., et al., "Peptide Hormone Covalently Bound to Polyelectrolytes and Embedded into Multilayer Architectures Conserving Full Biological Activity," *Biomacromolecules*, 2001, pp. 800-805, vol. 2, No. 3.

Dai, J., et al., "Controlling the Permeability of Multilayered Polyelectrolyte Films Through Derivatization, Cross-Linking, and Hydrolysis," *Langmuir*, 2001, pp. 931-937, vol. 17, No. 3.

Decher, G., "Fuzzy Nanoassemblies: Toward Layered Polymeric Multicomposites," *Science*, Aug. 29, 1997, pp. 1232-1237, vol. 277.

Decher, G., "Polyelectrolyte Multilayers, An Overview," *Multilayer Thin Films*, 2002, pp. 1-46.

Dubas, S.T., et al., "Swelling and Smoothing of Polyelectrolyte Multilayers by Salt," *Langmuir*, 2001, pp. 7725-7727, vol. 17, No. 25.

Durstock, M.F., et al., "Dielectric Properties of Polyelectrolyte Multilayers," *Langmuir*, 2001, pp. 7865-7872, vol. 17, No. 25.

Elbert, D.L., et al., "Thin Polymer Layers Formed by Polyelectrolyte Multilayer Techniques on Biological Surfaces," *Langmuir*, 1999, pp. 5355-5362, vol. 15, No. 16.

Farhat, T.R., et al., "Doping-Controlled Ion Diffusion in Polyelectrolyte Multilayers: Mass Transport in Reluctant Exchangers," *Journal of the American Chemical Society*, 2003, pp. 4627-4636, vol. 125, No. 15.

Farhat, T.R., et al., "Ion Transport and Equilibria in Polyelectrolyte Multilayers," *Langmuir*, 2001, pp. 1184-1192, vol. 17, No. 4.

Fou, A.C., et al., "Fabrication and Properties of Light-Emitting Diodes Based on Self-Assembled Multilayers of Poly(phenylene vinylene)," *J. Appl. Phys.*, May 15, 1996, pp. 7501-7509, vol. 79, No. 10.

Graul, T.W., et al., "Capillaries Modified by Polyelectrolyte Multilayers for Electrophoretic Separations," *Analytical Chemistry*, Sep. 15, 1999, pp. 4007-4013, vol. 71, No. 18.

Halayko, A.J., et al., "Plasticity in Skeletal, Cardiac, and Smooth Muscle Invited Review: Molecular Mechanisms of Phenotypic Plasticity in Smooth Muscle Cells," *J. Appl. Physiol.*, 2001, pp. 358-368, vol. 90.

Hammond, P.T., et al., "Formation of Polymer Microstructures by Selective Deposition of Polyion Multilayers Using Patterned Self-Assembled Monolayers as a Template," *Macromolecules*, 1995, pp. 7569-7571, vol. 28, No. 22.

Harris, J.J., et al., "Electrochemical and in Situ Ellipsometric Investigation of the Permeability and Stability of Layered Polyelectrolyte Films," *Langmuir*, 2000, pp. 2006-2013, vol. 16, No. 4.

Harris, J.J., et al., "Layered Polyelectrolyte Films as Selective, Ultrathin Barriers for Anion Transport," *Chem. Mater.*, 2000, pp. 1941-1946, vol. 12, No. 7.

Harris, J.J., et al., "Synthesis of Passivating, Nylon-Like Coatings Through Cross-Linking of Ultrathin Polyelectrolyte Films," *Journal of the American Chemical Society*, 1999, pp. 1978-1979, vol. 121, No. 9, American Chemical Society.

Holmlin, R.E., et al., "Zwitterionic SAMs that Resist Nonspecific Absorption of Protein from Aqueous Buffer," *Langmuir*, 2001, pp. 2841-2850, vol. 17, No. 9.

Hsieh, M.C., et al., "Surface "Priming" for Layer-by-Layer Deposition: Polyelectrolyte Multilayer Formation on Allylamine Plasma-Modified Poly(tetrafluoroethylene)," *Macromolecules*, 1997, pp. 8453-8458, vol. 30, No. 26.

Huck, W.T.S., et al., "Patterned Polymer Multilayers as Etch Resists," *Langmuir*, 1999, pp. 6862-6867, vol. 15, No. 20.

Hyde, F.W., et al., "Comparison of Fluorinated Polymers Against Stainless Steel, Glass and Polypropylene in Microbial Biofilm Adherence and Removal," *Journal of Industrial Microbiology & Biotechnology*, 1997, pp. 142-149, vol. 19.

Ichinose, I., et al., "Electrostatic Absorption of Cytochrome c on Ultrathin $ZrO_2$-Gel Layers and Preparation of Alternate Multilayers," *Langmuir*, 2003, pp. 3883-3888, vol. 19, No. 9.

Indolfi, C., et al., "Molecular Mechanisms of In-Stent Restenosis and Approach to Therapy with Eluting Stents," *Trends Cardiovasc. Med.*, 2003, pp. 142-148, vol. 13, No. 4.

Ito, Y., et al., "Micropatterned Immobilization of Epidermal Growth Factor to Regulate Cell Function," *Bioconjugate Chem.*, 1998, pp. 277-282, vol. 9, No. 2.

Jessel, N., et al., "Bioactive Coatings Based on a Polyelectrolyte Multilayer Architecture Functionalized by Embedded Proteins," *Advanced Materials*, May 2, 2003, pp. 692-695, vol. 15, No. 9.

Jiang, X., et al., "Selective Deposition in Layer-by-Layer Assembly: Functional Graft Copolymers as Molecular Templates," *Langmuir*, 2000, pp. 8501-8509, vol. 16, No. 22.

Jorgenson, J.W., et al., "Zone Electrophoresis in Open-Tubular Glass Capillaries," *Analytical Chemistry*, Jul. 1981, pp. 1298-1302, vol. 53, No. 8.

Knight, A.W., et al., "Occurrence, Mechanisms and Analytical Applications of Electrogenerated Chemiluminescence, A Review," *Analyst.*, May 1994, pp. 879-890, vol. 119.

Kozlovskaya, V., et al., "Hydrogen-Bonded Polymer Capsules Formed by Layer-by-Layer Self-Assembly," *Macromolecules*, 2003, pp. 8590-8592, vol. 36, No. 23.

Krasemann, L., et al., "Selective Ion Transport Across Self-Assembled Alternating Multilayers of Cationic and Anionic Polyelectrolytes," *Langmuir*, 2000, pp. 287-290, vol. 16, No. 2.

Ladam, G., et al., "Protein Absorption onto Auto-Assembled Polyelectrolyte Films," *Langmuir*, 2001, pp. 878-882, vol. 17, No. 3.

Ladam, G., et al., "Protein Interactions with Polyelectrolyte Multilayers: Interactions Between Human Serum Albumin and Polystyrene Sulfonate/Polyallylamine Multilayers," *Biomacromolecules*, 2000, pp. 674-687, vol. 1, No. 4.

Lahav, M., et al., "Tailored Chemosensors for Chloroaromatic Acids Using Molecular Imprinted $TiO_2$ Thin Films on Ion-Sensitive Field-Effect Transistors," *Analytical Chemistry*, Feb. 1, 2001, pp. 720-723, vol. 73, No. 3.

Laurent, D., et al., "Multilayer Assemblies of Redox Polyelectrolytes," *Langmuir*, 1997, pp. 1552-1557, vol. 13, No. 6.

Leväsalmi, J.M., et al., "Poly(4-methyl-1-pentene)-Supported Polyelectrolyte Multilayer Films: Preparation and Gas Permeability," *Macromolecules*, 1997, pp. 1752-1757, vol. 30, No. 6.

Lösche, M., et al., "Detailed Structure of Molecularly Thin Polyelectrolyte Multilayer Films on Solid Substrates as Revealed by Neutron Reflectometry," *Macromolecules*, 1998, pp. 8893-8906, vol. 31, No. 25.

Lvov, Y., et al., "Assembly of Multicomponent Protein Films by Means of Electrostatic Layer-by-Layer Absorption," *Journal of the American Chemical Society*, 1995, pp. 6117-6123, vol. 117, No. 22, American Chemical Society.

Lvov, Y., et al., "Biocolloids with Ordered Urease Multilayer Shells as Enzymatic Reactors," *Analytical Chemistry*, Sep. 1, 2001, pp. 4212-4217, vol. 73, No. 17.

Lvov, Y.M., et al., "Direct Electrochemistry of Myoglobin and Cytochrome $P450_{cam}$ in Alternate Layer-by-Layer Films with DNA and Other Polyions," *Journal of the American Chemical Society*, 1998, pp. 4073-4080, vol. 120, No. 17, American Chemical Society.

Mamedov, A.A., et al., "Free-Standing Layer-by-Layer Assembled Films of Magnetite Nanoparticles," *Langmuir*, 2000, pp. 5530-5533, vol. 16, No. 13.

Mendelsohn, J.D., et al., "Fabrication of Microporous Thin Films from Polyelectrolyte Multilayers," *Langmuir*, 2000, pp. 5017-5023, vol. 16, No. 11.

Mendelsohn, J.D., et al., "Rational Design of Cytophilic and Cytophobic Polyelectrolyte Multilayer Thin Films," *Biomacromolecules*, 2003, pp. 96-106, vol. 4, No. 1.

Möhwald, H., et al., "Smart Capsules," *Multilayer Thin Films*, 2002, pp. 363-392.

Mrksich, M., et al., "Surface Plasmon Resonance Permits in Situ Measurement of Protein Absorption on Self-Assembled Monolayers of Alkanethiolates on Gold," *Langmuir*, 1995, pp. 4383-4385, vol. 11, No. 11.

Müller, M., et al., "Deposition and Properties of Polyelectrolyte Multilayers Studied by ATR-FTIR Spectroscopy," *Materials Science and Engineering C8-9*, 1999, pp. 163-169.

Müller, M., et al., "Polyelectrolyte Complex Layers: A Promising Concept for Anti-Fouling Coatings Verified by in-situ ATR-FTIR Spectroscopy," *Macromolecular Rapid Communications*, 1999, pp. 607-611, vol. 20.

Müller, M., et al., "Selective Interaction Between Proteins and the Outermost Surface of Polyelectrolyte Multilayers: Influence of the Polyanion Type, pH and Salt," *Macromolecular Rapid Communications*, 2001, pp. 390-395, vol. 22.

Onda, M., et al., "Sequential Actions of Glucose Oxidase and Peroxidase in Molecular Films Assembled by Layer-by-Layer Alternate Absorption," *Biotechnology and Bioengineering*, Jul. 20, 1996, pp. 163-167, vol. 51, No. 2.

Öner, D., et al., "Ultrahydrophobic Surfaces. Effects of Topography Length Scales on Wettability," *Langmuir*, 2000, pp. 7777-7782, vol. 16, No. 20.

Ostuni, E., et al., "Self-Assembled Monolayers That Resist the Absorption of Proteins and the Adhesion of Bacterial and Mammalian Cells," *Langmuir*, 2001, pp. 6336-6343, vol. 17, No. 20.

Overberger, C.G., et al., "Imidazole-Containing Polymers. Synthesis and Polymerization of the Monomer 4(5)-Vinylimidazole," *Journal of the American Chemical Society*, Apr. 5, 1963, pp. 951-955, vol. 85, American Chemical Society.

Pei, R., et al., "Assembly of Alternating Polycation and DNA Multilayer Films by Electrostatic Layer-by-Layer Absorption," *Biomacromolecules*, 2001, pp. 463-468, vol. 2, No. 2.

Richert, L., et al., "Cell Interactions with Polyelectrolyte Multilayer Films," *Biomacromolecules*, 2002, pp. 1170-1178, vol. 3, No. 6.

Richert, L., et al., "Layer by Layer Buildup of Polysaccharide Films: Physical Chemistry and Cellular Adhesion Aspects," *Langmuir*, 2004, pp. 448-458, vol. 20, No. 2.

Rosidian, A., et al., "Ionic Self-Assembly of Ultrahard $ZrO_2$/Polymer Nanocomposite Thin Films," *Advanced Materials*, 1998, pp. 1087-1091, vol. 10, No. 14.

Salloum, D.S., et al., "Protein Absorption Modalities on Polyelectrolyte Multilayers," *Biomacromolecules*, 2004, pp. 1089-1096, vol. 5, No. 3.

Schlenoff, J.B., et al., "Sprayed Polyelectrolyte Multilayers," *Langmuir*, 2000, pp. 9968-9969, vol. 16, No. 26.

Schwinté, P., et al., "Stabilizing Effects of Various Polyelectrolyte Multilayer Films on the Structure of Absorbed/Embedded Fibrinogen Molecules: An ATR-FTIR Study," *J. Phys. Chem. B*, 2001, pp. 11906-11916, vol. 105, No. 47.

Serizawa, T., et al., "Alternating Bioactivity of Polymeric Layer-by-Layer Assemblies: Anticoagulation vs Procoagulation of Human Blood," *Biomacromolecules*, 2002, pp. 724-731, vol. 3, No. 4.

Stepp, J., et al., "Electrochromism and Electrocatalysis in Viologen Polyelectrolyte Multilayers," *Journal of the Electrochemical Society*, Jun. 1997, pp. L155-L157, vol. 144, No. 6.

Stroeve, P., et al., "Gas Transfer in Supported Films Made by Molecular Self-Assembly of Ionic Polymers," *Thin Solid Films 284-285*, 1996, pp. 708-712.

Sukhishvili, S.A., et al., "Layered, Erasable Polymer Multilayers Formed by Hydrogen-Bonded Sequential Self-Assembly," *Macromolecules*, 2002, pp. 301-310, vol. 35, No. 1.

Szleifer, I., "Polymers and Proteins: Interactions at Interfaces," *Current Opinion in Solid State Material Science Biomaterials*, 1997, pp. 337-344.

Thierry, B., et al., "Bioactive Coatings of Endovascular Stents Based on Polyelectrolyte Multilayers," *Biomacromolecules*, 2003, pp. 1564-1571, vol. 4, No. 6.

Tieke, B., et al., "Ultrathin Self-Assembled Polyelectrolyte Multilayer Membranes," *The European Physical Journal E*, 2001, pp. 29-39, vol. 5.

Worth, N.F., et al., "Vascular Smooth Muscle Cell Phenotypic Modulation in Culture is Associated With Reorganisation of Contractile and Cytoskeletal Proteins," *Cell Motility and the Cytoskeleton*, 2001, pp. 130-145, vol. 49.

Yoo, D., et al., "Controlling Bilayer Composition and Surface Wettability of Sequentially Absorbed Multilayers of Weak Polyelectrolytes," *Macromolecules*, 1998, pp. 4309-4318, vol. 31, No. 13.

Zou, H., et al., "Monolithic Stationary Phases for Liquid Chromatography and Capillary Electrochromatography," *Journal of Chromatography A*, 2002, pp. 5-32, vol. 954.

CONTROLLED TRANSPORT THROUGH MULTIPLE REVERSIBLE INTERACTION POINT MEMBRANES

CROSS-REFERENCE TO RELATED APPLICATIONS

This application is a continuation of U.S. application Ser. No. 11/085,926, now U.S. Pat. No. 7,238,536 entitled CONTROLLED TRANSPORT THROUGH MULTIPLE REVERSIBLE INTERACTION POINT MEMBRANES and filed Mar. 22, 2005, which claims priority from U.S. provisional application Ser. No. 60/555,394, filed on Mar. 22, 2004.

STATEMENT REGARDING FEDERALLY SPONSORED RESEARCH

This invention was made with Government support under Grant DMR 9727717 awarded by the National Science Foundation. The Government has certain rights in this invention.

BACKGROUND OF THE INVENTION

The present invention relates to the field of membrane transport, particularly to the control over membrane transport of one species by another, and, more particularly, to the control of transport through a membrane covering a sensing element.

Transduction of a physical stimulus into a current or a voltage that may be read by standard electronic circuits is an essential component of measurement science. A device that responds in a quantitative fashion to the presence of a particular chemical species, or a class of chemical species, is known as a sensor. Sensors respond to chemical species dispersed throughout liquid, in particular aqueous, or gaseous media. The preferred requirements for sensors are several: they respond rapidly, and with high sensitivity and selectivity. Sensors are also preferably stable, yield reproducible, reversible response, are relatively easy to calibrate, and are compact.

Since most species to be measured by sensors are mixed with many other species, there is a need for sensors to be selective. Selectivity is an enhanced response for one particular species, or class of species, in the presence of others. Sensors often comprise a measuring element, such as an electrode, covered with a material designed to impart selective transport of a chemical species to be detected. For example, yttrium-doped zirconia, an oxide ion conducting material (see Schwank and DiBattista, Materials Research Society Bulletin, 24, 44 (1999)), is widely used in the automotive industry to sense oxygen concentration in engines.

Sensors in contact with gases or liquids, water in particular, frequently rely on a polymeric membrane coating for providing selectivity. The membrane may be designed to allow selective passage of a species across the membrane to a responsive element behind the membrane. For example, Prohaska et al. (U.S. Pat. No. 6,682,638) disclose a miniaturized sensor comprising a polymer ionomer coating an electrode for detecting species in the gas or vapor phase. The Clark oxygen electrode (see Sawyer et al. *Electrochemistry for Chemists*, $2^{nd}$ ed, Wiley, New York, 1995) comprises a semipermeable fluoropolymer membrane across which oxygen, dissolved in solution, can diffuse and initiate an electrochemical reaction at a platinum electrode. Electrodes selective for ions may be constructed by immobilizing an ion exchanger within a polymer membrane, or a thin film liquid sandwiched between two polymeric membranes. A comprehensive list of such electrodes described up to 1990 can be found in Umezawa, Handbook of Ion-Selective Electrodes Selectivity Coefficients; CRC Press: Boca Raton, Ann Arbor, Boston, 1990. The membranes are typically based on a polymer such as polyvinyl chloride (PVC) or a polyurethane and usually also contain a water immiscible organic liquid which has plasticizer properties.

Alternatively, the surface of the membrane is modified to permit selective interaction with a chemical species, or a class of chemical species.

Membranes formed by casting, dip coating, spraying or other means mainly rely on nonspecific interactions, such as van der Waals, crystal packing interactions, and insolubility in water. For example, a membrane of PVC may be formed over an electrode by casting or dip coating. PVC, being insoluble in water, remains intact in contact with aqueous solutions. Membranes made from materials that tend to be less mechanically stable in contact with their sensing media are often stabilized by the introduction of chemical crosslinking. These crosslinks are introduced, during the deposition, or post-deposition, by irreversible chemical reactions.

Recently, membranes comprising two or more component polymeric materials (including biomacromolecules) that are held together by interactions of a more determinate nature have been described. These membranes are prepared using at least two component polymeric materials which are alternately deposited on a substrate or substratum. Each deposition deposits a layer of material, and the membrane is thus often termed a "multilayer." See Decher and Schlenoff, Eds., *Multilayer Thin Films—Sequential Assembly of Nanocomposite Materials*, Wiley-VCH, Weinheim (2003); Decher, *Science*, 277, 1232 (1997). The component polymeric materials interact at specific points along the polymeric molecules. These interactions are reversible, and the membranes, or thin films that are made are therefore termed Multiple Reversible Interaction Point Membranes, MRIPMs. Reversible interaction types employed for MRIPMs include electrostatic or ion pairing interactions, hydrogen bonding, base pairing in nucleic acids, polar acid-base interactions, charge transfer interactions and hydrophobic interactions. Combinations of these interactions have also been employed for making MRIPMs. Interactions between interaction points on component polymeric materials effectively form a plurality of physical crosslink points, which act cooperatively to hold the membrane together.

Preferred interactions are electrostatic, or ion pairing, interactions between polyelectrolytes. Polyelectrolytes are macromolecules comprising a plurality of charged repeat units. Amorphous complexes may be formed by contacting solutions of polyelectrolytes bearing opposite charges (see Dautzenberg et al. *Polyelectrolytes. Formation, Characterization and Application*, Hanser, Munich, 1994). The driving force for association, or complexation, of polyelectrolytes is multiple ion pairing between oppositely charged repeat units on different molecules. These same driving forces are employed for preparing membranes, or thin films, of polyelectrolyte complex. Decher and Hong (U.S. Pat. No. 5,208,111) disclose a method for a buildup of multilayers by alternating dipping, i.e., cycling a substrate between two reservoirs containing aqueous solutions of polyelectrolytes of opposite charge, with an optional rinse step in polymer-free solution following each immersion. Each cycle adds a layer of polymer via ion pairing forces to the oppositely-charged surface and reverses the surface charge thereby priming the film for the addition of the next layer. Films prepared in this manner tend to be uniform, follow the contours and irregularities of the substrate, and are typically between about 10 nm and about 10,000 nm thick. The thickness of a film depends on many factors, including the number of layers deposited, the ionic strength of the solutions, the types of polymers, the deposition time, the solution pH, the temperature, and the solvent used. Although studies have shown that substantial interpenetration of the individual polymer layers results in little composition variation over the thickness of a film, such polymer thin films are, nevertheless, referred to as polyelectrolyte multilayers (PEMUs). PEMUs are a subset of MRIPMs.

Though recently developed, PEMUs are being used in a wide variety of fields including light emitting devices, nonlinear optics, sensors, enzyme active thin films, electrochromics, conductive coatings, patterning, anticorrosion coatings, antistatic coatings, lubricating films, biocompatibilization, dialysis, and as selective membranes for the separation of gaseous and dissolved ionic species. See Fou et al., *J. Appl. Phys.*, 79, 7501 (1996); Decher et al., *J. Biosens. Bioelect.* 9, 677 (1994); Sun et al., *Macromol. Chem. Phys.* 197, 147 (1996); Onda et al., *Biotech Bioeng.* 51, 163 (1996); Lvov et al., *J. Am. Chem. Soc.* 120, 40733 (1998); Laurent et al., *Langmuir* 13, 1552 (1997); Stepp et al., *J. Electrochem. Soc.* 144, L155 (1997); Cheung et al., *Thin Solid Films* 244, 985 (1994); Hammond et al., *Macromolecules* 28, 7569 (1995); Huck et al., *Langmuir* 15, 6862 (1999); Stroeve et al., *Thin Solid Films* 284, 708 (1996); Levasalmi et al., *Macromolecules* 30, 1752 (1997); Harris et al., *Langmuir* 16, 2006 (2000); Krasemann et al., *Langmuir* 16, 287 (2000); Harris et al., *J. Am. Chem. Soc.* 121, 1978 (1999); Harris et al., *Chem. Mater.* 12, 1941 (2000).

Polyelectrolyte complexes are known to moderate interactions with biological systems, usually with the purpose of rendering an article or object inert to biological activity. That is, a coating of polyelectrolyte complex does not elicit undesirable inflammation or immune responses. Fine tuning of protein adsorption at the solid/liquid interface is critical in certain areas of materials science and biomedical engineering. Systems for delivery or biosensors, for example, bear modified surfaces designed to enhance or minimize protein adsorption. The latter goal is generally desirable for blood-contacting devices, chromatographic supports, contact lenses, and immunoassays, to name a few. Due to their ease of use and water compatibility, PEMUs have been investigated as surface-modifying agents for protein interactions (see Ladam, G.; Gergely, C.; Senger, B.; Decher, G.; Voegel, J. C.; Schaaf, P.; Cuisinier, F. J. G. *Biomacromolecules* 1, 674 (2000)). For example, polyelectrolyte complexes have been coated on Islets of Langerhans, an insulin-producing biological apparatus, to make them more acceptable when implanted in vivo (see O'Shea and Sun, *Diabetes* 35, 953 (1986) and Goosen et al. U.S. Pat. No. 4,673,566 (1987)). In another example, an ocular contact lens treated with a polyelectrolyte complex improves the properties of the lens (see Ellis and Salamone, U.S. Pat. No. 4,168,112 (1979)). Winterton et al. (U.S. Pat. No. 6,451,871 (2002)) disclose a method of making polyelectrolyte complexes on the surface of a contact lens by the multilayering method.

The rate of transport of species across MRIPMs, when they are used as sensors, and for other applications, is determined by a variety of factors. For PEMUs, one of these factors is whether there are sites available within the membrane to accommodate a particular species that is traversing the membrane. Creation of sites for transport within PEMUs has been termed "doping" and has been accomplished by the addition of salt (NaCl). See Farhat and Schlenoff, *Langmuir*, 17, 1184 (2001).

Coordinated experimental and theoretical studies have been carried out to ascertain how ion transport though polyelectrolyte complex is reversibly regulated by solution ionic strength (see Farhat and Schlenoff, *J. Am. Chem. Soc.*, 125, 4627 (2003)). In the presence of external salt species (such as NaCl), ions are forced into the soft material, which becomes an ion exchanger/transporter. For n Pol$^+$Pol$^-$ polyelectrolyte ion pairs, this reversible process is represented by:

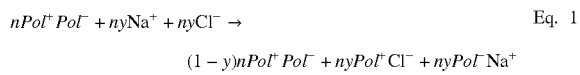

$$nPol^+Pol^- + nyNa^+ + nyCl^- \rightarrow$$
$$(1-y)nPol^+Pol^- + nyPol^+Cl^- + nyPol^-Na^+$$

Eq. 1 where y is the doping level, or the fraction of Pol$^+$Pol$^-$ pairs converted to Pol$^+$Cl$^-$ and Pol$^-$Na$^+$ transporting sites. The driving force for doping is reversible chemical potential, controlled directly by concentration. The doping reaction summarized by this equation creates randomly distributed clusters of sites—"defects" among which ions may hop. Transport is favored for ions of lower charge and the diffusion rate is a strong nonlinear function of doping level—both Monte Carlo and continuum probability theoretical approaches predict this trend.

Electrogenerated chemiluminescence, ECL, also known as electroluminescence, is a technique whereby a species is oxidized or reduced at an electrode to yield a product that is in an excited, or high-energy state. During relaxation of this excited state, light is generated, which may be detected by a light sensitive instrument, such as a photomultiplier, photodiode, photodiode array, or charged coupled device. Often, additional reagents are required to promote more efficient emission of light. Several reviews on the topic are available (see Faulkner and Bard, *Electroanalytical Chemistry* 10, 1, 1977). See also U.S. Pat. Nos. 5,068,088, 5,093,268, 5,061, 445, 5,238,808, 5,147,806, 5,247,243, 5,296,191, 5,310,687, 5,221,605.

Many ECL systems comprise modified electrodes. For example, Dixon et al. (U.S. Pat. No. 5,075,172) disclose an electroluminescent layer comprising a charged fluorinated polymer coating an electrode, which traps an electroluminescent species. Zhang and Bard (U.S. Pat. No. 5,324,457) disclose an electrode coated with a nonpolymeric layer of electroluminescent material. The use of ECL in assays is reviewed in detail by, for example, Knight et al., *Analyst*, 119, 879 (1994).

SUMMARY OF THE INVENTION

Among the aspects of this invention may be noted is a method for controlling the passage of a chemical species A across a membrane by the addition of a chemical species B. Species A interacts selectively or nonselectively with said the membrane whereas species B interacts selectively with the membrane. The passage of species A is preferably detected by electrochemical means, by calorimetric or fluorescence means, or by electrogenerated chemiluminescence. The MRIPM functionality, which is selective with species A or B, may be diluted with unselective functionality, said dilution accomplished by mixing polymeric components comprising selective functionality and unselective functionality, both polymeric components having net negative or net positive charge, in one of the solutions used to deposit the MRIPM thin film. The MRIPMs of the present invention may be further modified to control the degree of adsorption of biomacromolecules, such as proteins, polypeptides, DNA or RNA, to said MRIPM by the introduction of functional groups known to resist such adsorption. The polymeric components comprising said adsorption-resistant functional groups also comprise multiply interacting functional groups to hold the MRIPM together.

Briefly, therefore, the present invention is directed to a method for causing a membrane to become permeable to a first chemical species. The method comprises contacting the membrane with a solution comprising a second chemical species, wherein (1) the membrane comprises a polyelectrolyte complex film, the polyelectrolyte complex film comprising a positively-charged polyelectrolyte and a negatively-charged polyelectrolyte, (2) the second chemical species selectively interacts with the membrane, and (3) selective interaction of the second chemical species with the membrane causes the membrane to become permeable to the first chemical species, thereby causing the first chemical species to permeate the membrane.

Other objects and aspects of the invention will be, in part, pointed out and, in part, apparent hereinafter.

DETAILED DESCRIPTION OF THE PREFERRED EMBODIMENT(S)

Figure 1:
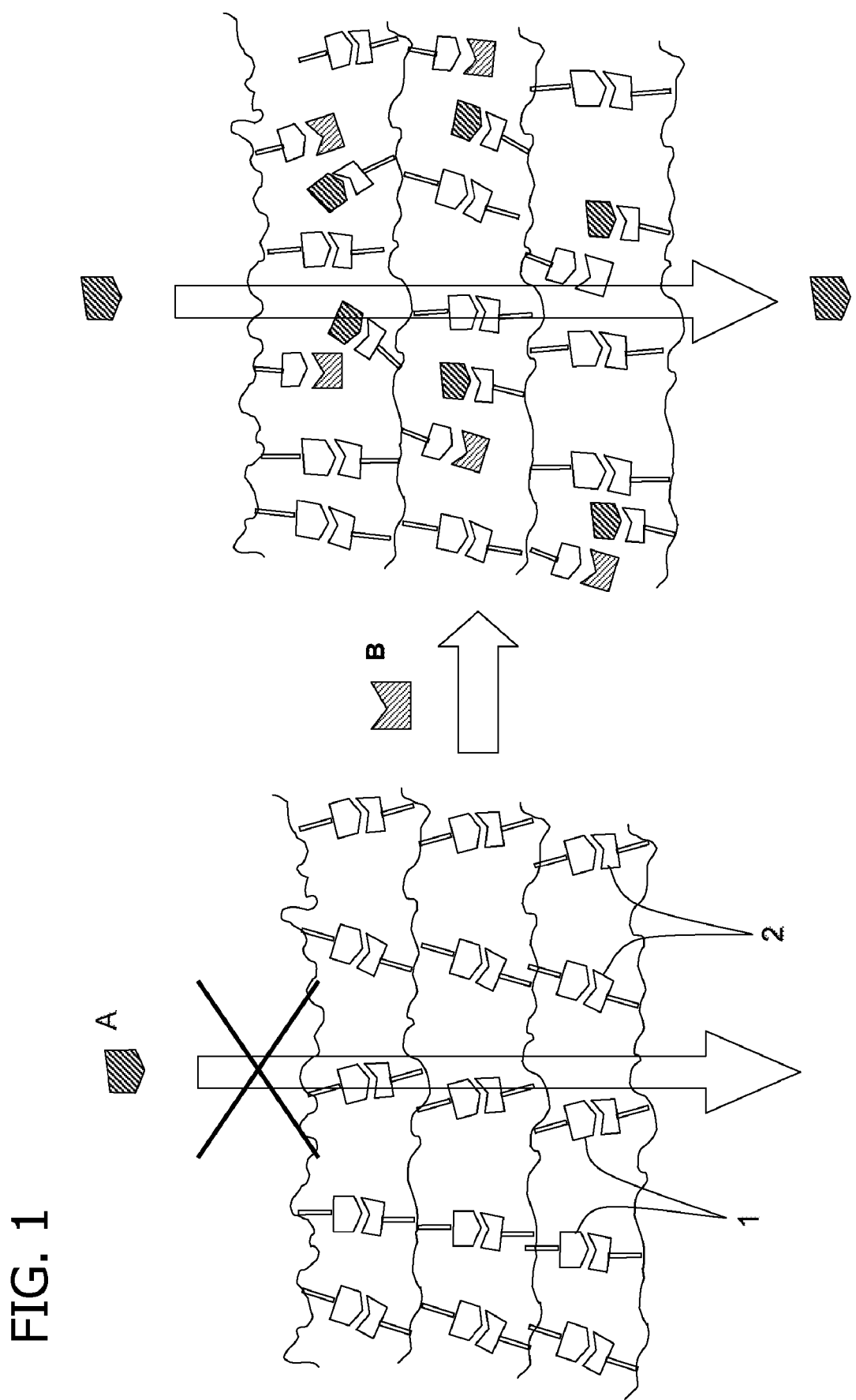
FIG. 1 is a schematic diagram representing the passage of species A through a MRIPM comprising reversible MRIPM interaction units 1 and 2. When units 1 and 2 are fully engaged, as in the diagram on the left, there are no sites within the membrane at which species A can reside. When selective species B is added, it interacts with unit 1 of the MRIPM, freeing up the complimentary unit 2 to interact with species A (right panel). Since A now has sites to reside in the membrane, A is now able to traverse the membrane (said travel is indicated by the large arrow).

One aspect of the present invention is to control the passage of a first species A through a membrane comprising a plurality of reversible interacting contacts. Said first species interacts with said interacting contacts in a selective or nonselective manner. A second species B also interacts with said interacting membrane contacts, but in a selective manner. The function of the second species is to create sites within the membrane for passage of the first species. If the measurement system responds directly to the first species, it therefore responds indirectly to the second species. The process is represented schematically in FIG. 1. FIG. 1 shows the passage of species A, having specific interaction, through a membrane comprising multiple reversible interacting units 1 and 2, each indicated by a "lock and key" matching of repeat units on different polymeric molecules. In FIG. 1, species A interacts with MRIPM unit 2. Species B also has a specific interaction, but the repeat units on the membrane with which B interacts are not the same as those that interact with A. In FIG. 1, species B interacts with MRIPM unit 1. Before the addition of species B, the MRIPM does not contain any available sites for species A. When B is added, it interacts with the MRIPM as shown, freeing up sites that are complimentary for A. A is thus able to move through the MRIPM by these sites. Examples of preferred interacting MRIPM units 1 and 2 interacting via the lock and key mechanism represented in FIG. 1, are: positive and negative charge; hydrogen bond donor and hydrogen bond acceptor; charge transfer donor and charge transfer acceptor; positive dipole and negative dipole; two complementary nucleic acid base pairs (adenine with thymine, or guanine and cytosine); two complimentary sequences of nucleic acid base pairs; two complimentary strands of peptides; and antibody and antigen. In this invention, B interacts selectively with the MRIPM such that a small amount of B creates many doping sites for transport of A.

Selective interaction of a species B with a membrane is known by those skilled in the art to manifest itself as an affinity of the membrane for the species. One quantitative measure of this affinity is the distribution coefficient, K, which is the ratio of concentration of species in the membrane to the concentration in solution at equilibrium. For the purposes of this invention, selective interaction is understood to occur when K is greater than about 2, preferably greater than about 10, and more preferably greater than about 100.

It is known by those skilled in the art that the creation of sites within the membrane by the second species is termed "doping." Doping reactions have been limited to species B being nonselective, generated, for example, by salt (see T. R. Farhat and J. B. Schlenoff, *Langmuir,* 17, 1184 (2001)). It is demonstrated here that the stronger the interaction of the second species B with the interacting contacts within the membrane, the more sites are created within the membrane to facilitate the passage of the first species A. Exemplary interactions may be polypeptide, proteins, polynucleotide, DNA, RNA, antibody/antigen, and enzyme/receptor.

Preferred membrane interactions for species A and species B are polyvalent. Polyvalent interactions between two entities occur when there are two or more points of interaction between these entities. Those skilled in the art will understand that polyvalent interactions act cooperatively and are therefore stronger, and potentially more selective, than monovalent, or single-point, interactions. Exemplary polyvalent interactions may be polypeptide, proteins, polynucleotide, DNA, RNA, antibody/antigen, and enzyme/receptor.

Preferred interactions between MRIPM and species A and B are selected from the group comprising electrostatic, ion pairing, nucleic acid base pairing, hydrogen bonding, peptide sequence pairing, and antibody-antigen pairing.

In one embodiment of this invention, the membrane is on the surface of and in contact with an electrically conductive substrate, species A is electrochemically active ("redox active") and species B is not redox active. Preferred substrates for electrochemical detection of species A comprise a thin conducting film on their surface, such as metals, preferably gold, palladium, silver, nickel, chromium and platinum, or semiconductors, preferably tin oxide. Carbon is another preferred electrically conductive substrate. Conductive substrates are preferably pretreated to enhance the adhesion of the membrane. Preferred treatments for oxides include reaction with siloxanes or chlorosilanes, such as aminosiloxanes, to impart negative or positive charges on the surface. Strongly adhering polyelectrolytes, such as poly(ethyleneimine), are alternative surface treatments. Preferred methods of enhancing adhesion of polynucleic acids or polypeptides on a noble metal surface, preferably gold, include the introduction of a sulfur-containing end group, preferably thiol.

In another embodiment of this invention, arrays of multiple electrodes are created on a substrate, each electrode individually addressable such that the electronic current may be individually measured. The preferred size for each electrode is an area approximately 1 to 1000 micrometers across, more preferably 10 to 100 micrometers across. When such an array is employed, each electrode is preferably covered by a MRIPM of different composition, each composition preferably being selective for a different species B.

Figure 2:
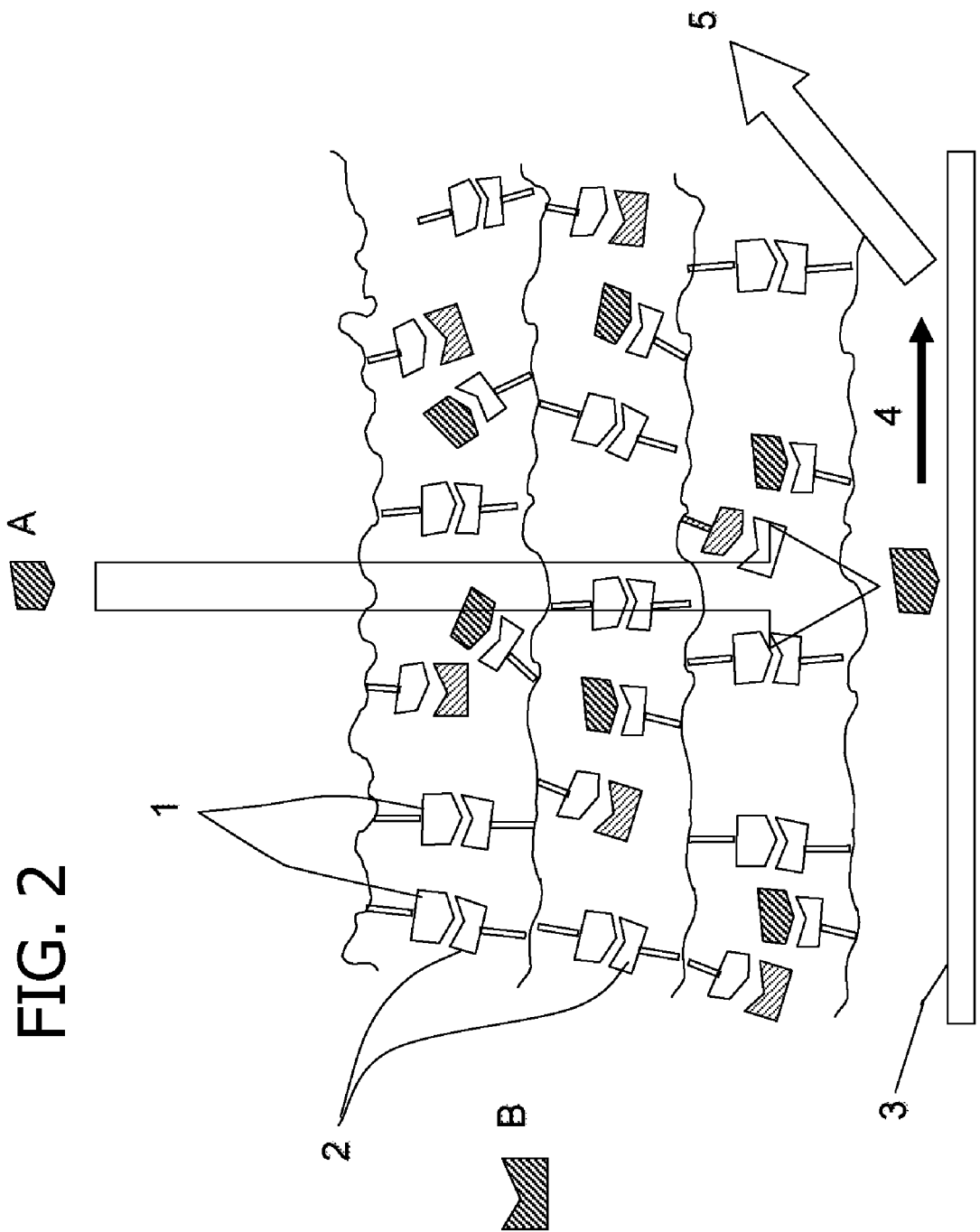
FIG. 2 is a scheme of electrogenerated chemiluminescence at a MRIPM comprising reversible interaction units 1 and 2 covering an electrode. Species A traverses the MRIPM upon addition of species B. On arriving at the electrode 3, species A undergoes electrochemistry 4, such as oxidation, which leads to the generation of light 5.

In yet another embodiment of this invention, passage of species A across the MRIPM is detected by electrogenerated chemiluminescence, ECL, of species A at an electrode, said electrode being behind and in contact with said membrane. ECL of species A traversing a MRIPM and generating light on arrival at the electrode is schematically represented in FIG. 2, which shows a scheme of electrogenerated chemiluminescence at a MRIPM comprising reversible interaction units 1 and 2 covering an electrode. Species A traverses the MRIPM upon addition of species B. On arriving at the electrode 3, species A undergoes electrochemistry 4, such as oxidation, which leads to the generation of light 5. Preferred species A for ECL are polyvalent and preferably have high efficiency for light output. Preferred ECL species are ruthenium bipyridine and derivatives thereof. The preferred potential at which the electrode is operated is that known by those skilled in the art to cause oxidation or reduction of the ECL species. The preferred method of detection of ECL at an electrode covered by a MRIPM is by a sensitive optical detector. Preferred optical detectors for ECL are photomultiplier and photodiode.

In another embodiment of this invention, the MRIPM comprises electroluminescent (ECL) functionality. Said ECL functionality is preferably bound to one of the polymeric components comprising the MRIPM. Preferred ECL functionality on said polymeric components are ruthenium pyridine and its derivatives. Preferred polymers to which said ECL functionality is bound are polyvinylpyridines, polyvinylimidazoles, and their derivatives and copolymers.

Preferably methods employing ECL also employ molecules known to enhance the light output efficiency of ECL. For example, oxalate ions and tertiary amines are known to those skilled in the art to enhance the ECL light output of ruthenium bipyridine derivatives (see Bard and Faulkner, *Electrochemical Methods: Fundamentals and Applications,* $2^{nd}$ Ed. Chapter 18, Wiley, New York 2001). In one embodiment of this invention, one or more of the polymeric components comprising the MRIPM also comprise tertiary amine units.

In another embodiment of this invention, an array of areas on a MRIPM is detected by electrogenerated chemiluminescence. Advantageously, such an array does not require individually addressable electrodes. Instead, a large area electrode is poised at the potential to cause ECL and individual areas are observed either one location at a time, or, preferably, all at one time with a 2-dimensional detector. A preferred 2-dimensional detector is a charged coupled device (CCD). When using an array optical detector, it is preferable to set up the MRIPM such that the correspondence between a pixel, or group of pixels, on the CCD and the exact chemical identity of the area of MRIPM imaged is known.

When using an area array of MRIPM on an electrode, it is preferable to subdivide the array into a plurality of regions having different chemical compositions, each region having different affinity to various possible species B. Preferably, the interaction between each species B and each corresponding area on the MRIPM array has a high degree of specificity. Preferably the chemical components on each area of the array are placed by micropatterning or microprinting methods known to those skilled in the art, including inkjet printing and microcontact printing or stamping.

Preferred electrical control at the substrate/MRIPM interface is achieved by scanning the voltage over a course of time and presenting the current-voltage, or current-time response, or fixing the voltage and observing the current as a function of time (chronopotentiometry). Chronopotentiometry is preferred when a species to be analyzed is passed over a membrane-covered electrode in a flow-through configuration.

For minimizing the size of the detection apparatus, it is preferable to use a series or network of microfluidic channels, such as those found on typical "lab-on-a-chip" modules, for handling injection and flow of liquid. Detection by an electrode covered with a MRIPM, using direct electrochemical measurement of current, or measurement by ECL, is preferred in such microfluidics systems.

When species B is a biopolymer comprising nucleic acids, such as DNA and RNA, it is preferred that the MRIPM also comprises nucleic acid. Preferably the membrane comprises sequences of nucleotides that are complimentary to the nucleotide sequences on the target molecules B to be detected. Such complementarity is understood by those skilled in the art to induce a high degree of selectivity between biomolecules comprising nucleotides.

When species B are polypeptides, proteins or enzymes, preferred MRIPMs comprise polypeptide sequences. Preferably the membrane comprises sequences of peptides that are complimentary to the sequences on the target molecules B. Such complimentarity is understood by those skilled in the art to induce a high degree of interaction or association between biomolecules comprising polypeptides. Such a high degree of interaction, when it is specific, is often termed "molecular recognition."

Preferred species A, in the case of multiple contact points comprising ion pairing groups, are charged, preferably with a net charge of greater than +2 or less than −2, more preferably with a net charge of greater than +3 or less than −3.

Preferred species A in the case of MRIPMs comprising nucleic acid are charged, preferably with a net charge of greater than +2 or −2, more preferably with a net charge of greater than +3 or −3.

Preferred species A in the case of MRIPMs comprising peptides are charged, preferably with a net charge of greater than +2 or −2, more preferably with a net charge of greater than +3 or −3.

In one embodiment of this invention, the MRIPM comprises functionality selective for metal ions. Preferred species conferring said selectivity are proteins, known by those skilled in the art for strongly binding with select metal ions. Preferred proteins are metalloenzymes, metallothioneins, and calmodulin (which binds strongly and selectively with calcium).

Those skilled in the art will recognize that a key feature of the invention disclosed herein is selective transport of a species, controlled by a second species, through a membrane or thin film. Once this transport has occurred, direct electrochemical, or indirect ECL detection are examples of many possible methods of registering the fact that a species has traversed a membrane. Thus, another preferred method of detecting transport of a species across a membrane is by placing an optically responsive molecule close to the substrate/membrane interface. In one embodiment of this invention, a color, visible to the eye, is generated by the reaction of species A and another chemical species located at the membrane/substrate interface. Such a reaction is known as a calorimetric reaction. In another embodiment of this invention, species A is a quencher of fluorescence and, having traversed the membrane, associates with a fluorescent molecule at the substrate/membrane interface, thereby quenching fluorescence. In another embodiment, species A instead enhances the fluorescence of a molecule found close to the substrate/membrane interface. The enhancement, in one embodiment, requires competitive displacement by species A of a molecule that is quenching fluorescence of another molecule found close to the substrate/membrane interface. Those skilled in the art will know that there are numerous combinations of fluorescent molecule/quencher. Some of these combinations, and methods for employing them, are described in Chapters 8 and 9 of *Principles of Fluorescence Spectroscopy*, $2^{nd}$ Ed., by J. R. Lakowicz, Kluwer Academic, New York, 1999.

In one embodiment of this invention, the MRIPM comprises a stratum selective for species B, and one or more strata that are not selective for species B. In yet another embodiment of this invention, a top stratum in contact with solution is selective for species B, while a bottom stratum in contact with the substrate comprises fluorescent material, preferably bound to one of the polymeric component comprising the membrane. Preferably fluorescence of said bottom stratum is quenched on arrival of species A.

A. Polyelectrolytes for Multilayer Films

The oppositely charged polymers (i.e., polyelectrolytes) used to form the films are water and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly(diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive and negative repeat units distributed throughout the polymer in a random, alternating or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic.

An example of a zwitterionic repeat unit is 3-[2-(acrylamido)-ethyldimethyl ammonio] propane sulfonate, AEDAPS. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units.

The charges on a polyelectrolyte may be derived directly from the monomer units or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($-SO_3^-$), such as poly(styrenesulfonic acid) (PSS), poly(2-acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof; polycarboxylates such as poly (acrylic acid) (PAA) and poly(methacrylic acid), polyphosphates and polyphosphonates.

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH) and polyethyleneimine (PEI); polysulfoniums and polyphosphoniums.

Some synthetic polyelectrolytes used in accordance with the present invention generally become charged at certain pH values. For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte at the surface of, or within, a polyelectrolyte multilayer.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

Further examples of oppositely-charged polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule comprises a protonated sub-unit (e.g., protonated amines). Some negatively charged biomacromolecules comprise a deprotonated sub-unit (e.g., deprotonated carboxylates or phosphates). Examples of biomacromolecules which may be charged for use in accordance with the present invention include proteins, polypeptides, enzymes, DNA, RNA, heparin, alginic acid, chondroitin sulfate, chitosan, chitosan sulfate, cellulose sulfate, polysaccharides, dextran sulfate, carrageenin, sulfonated lignin, and carboxymethylcellulose.

Natural, or biological, polyelectrolytes typically exhibit greater complexity in their structure than synthetic polyelectrolytes. For example, proteins may comprise any combination of about 2 dozen amino acid building blocks. Polymeric nucleic acids such as DNA and RNA may also comprise many different monomer repeat units. The sign and magnitude of the charge on proteins depends on the solution pH, as the charge on proteins is carried by weak acids, such as carboxylates (—COOH), or weak bases, such as primary, secondary, and tertiary amines. Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte typically comprises about 0.01% to about 40% by weight of a polyelectrolyte solution, and preferably about 0.1% to about 10% by weight.

Many of the foregoing polymers/polyelectrolytes, such as PDADMA and PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention.

Many of the foregoing polyelectrolytes have a very low toxicity. In fact, poly(diallyldimethylammonium chloride), poly(2-acrylamido-2-methyl-1-propane sulfonic acid) and their copolymers are used in the personal care industry, e.g., in shampoos. Also, because the polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Since some solvents are known to be incompatible with some plastic materials, preferred solvents for depositing polyelectrolyte complex thin films on plastics are water and alcohols.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), and protonated polyamines, such as, poly(allylamine hydrochloride) and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonic acid), poly(diallyldimethylammonium chloride), poly(N-methylvinylpyridinium) and poly(ethyleneimine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

In one embodiment of this invention, the charged polyelectrolyte is a synthetic copolymer comprising two or more charged repeat units, at least one of the repeat units being pH sensitive and the other repeat unit being pH insensitive, that is, maintaining the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

It is understood that the term "pH sensitive," as applied to functional groups, refers to functional groups that exhibit differing degrees of ionization over the working pH range of the experiment, while pH insensitive refers to functional groups that maintain the same charge (either positive or negative) over the working pH range of the experiment.

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly (acrylic acids), poly(methacrylic acids), poly(carboxylic acids), and copolymers thereof. Additional preferred polyelectrolytes comprise protonatable nitrogens, such as poly (pyridines), poly(imidazoles), poly(piperidines), and poly (amines) bearing primary, secondary or tertiary amine groups, such as poly(allylamine). Exemplary polyelectrolyte repeat units which are pH sensitive are shown in Table I.

TABLE I pH Sensitive Polyelectrolyte Repeat Units for Building PEMUs

| Name | Structure |
|---|---|
| Acrylic acid (PAA) | COOH |
| Allylamine (PAH) | $\overset{+}{N}H_3$ |
| 2-vinylpyridinium (P2VP) | (pyridine ring structure) |
| 4-vinylimidazole (PVI) | (imidazole ring structure with NH, N) |
| Amines | —$NR_1R_2R_3$ where $R_1$, $R_2$, and $R_3$ are independently hydrogen, alkyl, or aryl groups |

To avoid disruption, and possible decomposition, of the polyelectrolyte complex films preferred polyelectrolytes are copolymers comprising both pH sensitive and pH insensitive charged functionality on the same molecule. In one embodiment the negatively charged pH insensitive charged repeat unit comprising a polyelectrolyte is selected from the group consisting of styrenesulfonic acid, 2-acrylamido-2-methyl-1-propane sulfonic acid, sulfonated lignin, ethylenesulfonic acid, methacryloxyethylsulfonic acid, sulfonated ether ether ketone, phosphate. In another embodiment the positively charged pH insensitive repeat unit comprising a polyelectrolyte is selected from the group consisting of diallyldimethylammonium, vinylbenzyltrimethylammonium, ionenes, acryloxyethyltrimethyl ammonium chloride, methacryloxy (2-hydroxy)propyltrimethyl ammonium, N-methylvinylpyridinium, other N-alkylvinyl pyridiniums, a N-aryl vinyl pyridinium, alkyl- or aryl imidazolium, sulfonium, or phosphonium. Exemplary polyelectrolyte repeat units which are pH insensitive are shown in Table II.

TABLE II pH Insensitive Polyelectrolyte Repeat Units for Building PEMUs

| Name | Structure |
|---|---|
| diallyldimethylammonium (PDADMA) | 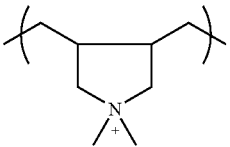 |
| styrenesulfonic acid (PSS) | 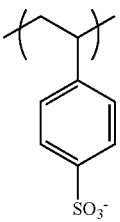 |
| 1-methyl-2-vinylpyridinium (PM2VP) | 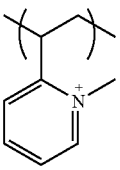 |

A range of positively charged and negatively charged pH-insensitive repeat units may be included in the predominantly positively charged polymer, the predominantly negatively charged polymer, or both. In one embodiment, the pH-insensitive repeat unit is a positively charged repeat unit selected from the group consisting of repeat units containing a quaternary nitrogen atom, a sulfonium ($S^+$) atom, or a phosphonium atom. Thus, for example, the quaternary nitrogen may be part of a quaternary ammonium moiety ($—N^+R_aR_bR_c$ wherein $R_a$, $R_b$, and $R_c$, are independently alkyl, aryl, or mixed alkyl and aryl), a pyridinium moiety, a bipyridinium moiety or an imidazolium moiety, the sulfonium atom may be part of a sulfonium moiety ($—S^+R_dR_e$ wherein $R_d$ and $R_e$ are independently alkyl, aryl, or mixed alkyl and aryl) and the phosphonium atom may be part of a phosphonium moiety ($—P^+R_fR_gR_h$ wherein $R_f$, $R_g$, and $R_h$ are independently alkyl, aryl, or mixed alkyl and aryl). In another embodiment, the pH-insensitive repeat unit is a negatively charged repeat unit selected from the group consisting of repeat units containing a sulfonate ($—SO_3^-$), a phosphate ($–OPO_3^-$), or a sulfate ($—SO_4^-$). For illustrative purposes, certain of these moieties are illustrated below:

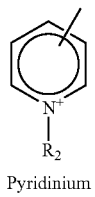

Pyridinium $R_2$ = alkyl or aryl

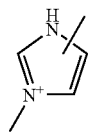

Imidazolium

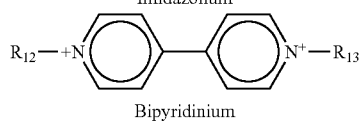

Bipyridinium $R_{12}$ and $R_{13}$ = alkyl or aryl

Preferred pH insensitive polyelectrolytes include polyelectrolytes comprising a sulfonate group ($—SO_3^-$), such as poly (styrenesulfonic acid) (PSS), poly(2-acrylamido-2-methyl-1-propane sulfonic acid) (PAMPS), sulfonated poly (ether ether ketone) (SPEEK), sulfonated lignin, poly(ethylenesulfonic acid), poly(methacryloxyethylsulfonic acid), their salts, and copolymers thereof; and polyelectrolytes comprising a quaternary ammonium group, such as poly(diallyldimethylammonium chloride) (PDADMA), poly(vinylbenzyltrimethylammonium) (PVBTA), ionenes, poly (acryloxyethyltrimethyl ammonium chloride), poly (methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof. In another embodiment the pH insensitive polyelectrolyte is selected from a group of polyelectrolytes that contain protonatable functionality, but that have pKa's outside the range of experimental use. For example, poly(ethyleneimine) has protonatable amine functionality with pKa in the range 8-10, and is thus fully charged (protonated) if the experimental conditions do not surpass a pH of about 7.

The preferred ratio of pH sensitive functional group to pH insensitive charged functional group enables control of surface and/or bulk charge without leading to disruption of the thin polyelectrolyte complex film. Thus ratios of pH sensitive functional group to pH insensitive charged functional group are preferably in the range 1:10 to 10:1, and more preferably in the range 2:10 to 10:2. Similarly, the total percentage of pH sensitive functional group is preferably between 5% and 95%.

Optionally, the polyelectrolytes comprise an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, ethylene oxide, and vinyl caprolactam. The structures of these uncharged repeat units are shown in Table III.

Protein adsorption is driven by the net influence of various interdependent interactions between and within surfaces and biopolymer. Possible protein-polyelectrolyte interactions can arise from 1) van der Waals forces 2) dipolar or hydrogen bonds 3) electrostatic forces 4) hydrophobic effects. Given the apparent range and strength of electrostatic forces, it is generally accepted that the surface charge plays a major role in adsorption. However, proteins are remarkably tenacious adsorbers, due to the other interaction mechanisms at their disposal. It is an object of this invention to show how surfaces may be selected to encourage or discourage the adsorption of proteins to MRIPMs when they are used as membranes for selective transport. Protein adsorption may be discouraged by copolymerizing with vinyl repeat units having hydrophilic groups, vinyl repeat units having zwitterionic groups, and hydrophilic repeat units.

It is also known by those skilled in the art that zwitterionic functional groups are also effective at resisting the adsorption of biomacromolecules, such as proteins (e.g. see Holmlin et al. *Langmuir*, 17, 2841 (2001)). In one embodiment of this invention, films of polyelectrolyte complex also comprise zwitterionic functional groups. It has been found that polymers comprising zwitterionic functional groups alone do not form polyelectrolyte complexes by the layer-by-layer technique if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. For control of bulk and surface charge of polyelectrolyte complexes, polyelectrolytes comprising zwitterionic groups also comprise pH sensitive units. These pH sensitive units are preferably acrylic acids, methacrylic acids, carboxylic acids, and copolymers thereof, and protonatable nitrogens, such as pyridines, imidazoles, piperidines, and primary, secondary, or tertiary amine groups, such as allylamine. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio] propane sulfonate) (PAEDAPS) and poly(N-propane sulfonate-2-vinyl pyridine) (P2PSVP). The structures of these zwitterions are shown in Table IV.

TABLE III

Neutral Repeat Units for use in PEMUs

| Name | Structure |
|---|---|
| acrylamide | (structure) |
| vinylpyrrolidone | (structure) |

TABLE III-continued

Neutral Repeat Units for use in PEMUs

| Name | Structure |
|---|---|
| vinylcaprolactam | (structure) |

TABLE IV

Zwitterionic Repeat Units for use in PEMUs

| Name | Structure |
|---|---|
| 3-[2-(acrylamido)-ethyldimethyl ammonio] propane sulfonate (AEDAPS) | (structure) |
| N-propane sulfonate-2-vinyl pyridine (2PSVP) | (structure) |

It has been disclosed by Graul and Schlenoff (*Anal. Chem.*, 71, 4007 (1999)) that polyelectrolyte thin films prepared by the multilayering method are able to control the adsorption of protein. The adsorption of basic proteins (that is, those with a positive net charge at the operating pH) is preferably minimized by terminating the polyelectrolyte complex film with a positive charge, which repels the positive proteins. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) Chemistry: Biotechnical and Biomedical Applications*, Plenum Press, New York, 1992). Yang and Sundberg (U.S. Pat. No. 6,660,367) disclose materials comprising ethylene glycol units that are effective at resisting the adsorption of hydrophilic proteins in microfluidic devices. In the present invention, copolymers of poly(ethylene oxide), PEO, or poly(ethylene glycol), PEG, are preferred materials for surface modification. The ethylene oxide (or ethylene glycol) repeat units are preferably present as blocks within a block copolymer. Preferably, the block copolymer also comprises blocks of charged repeat units, allowing the material to be incorporated into a polyelectrolyte complex. Sufficient ethylene oxide repeat units are required to promote resistance to protein adsorption, but too many ethylene oxide units do not allow polyelectrolyte complexes to associate. Therefore, the preferred ratio of charged to neutral blocks in a polyelectrolyte complex comprising a thin film for microfluidic flow control is from 10:1 to 1:4, and a more preferred ratio is 5:1 to 1:2.

In one preferred embodiment a small amount of chemical crosslinking is introduced into the MRIPM for stability. Crosslinking is preferably accomplished by including difunctional monomers in the polyelectrolytes comprising the thin film. For example, a divinyl repeat unit added to the polymerization reaction will be incorporated into two polyelectrolyte chains, giving a crosslink at the connection point. Alternatively, a polyelectrolyte film may be treated with a difunctional crosslinking agent. A preferred crosslinking agent is a dihalogenated compound, such as an aromatic or aliphatic dibromide, which is able to alkylate residual unalkylated units on two adjoining polyelectrolyte chains. Another preferred method of crosslinking a formed polyelectrolyte thin film is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (Macromolecules, 36, 8590 (2003)) is by the addition of a carbodiimide, which activates chemical crosslinking. The level of crosslinking is preferably 0.01 percent to 50%, and more preferably 0.1% to 10%.

B. Additives for Use in Building MRIPMs

The MRIPMs of the present invention may be built by incorporating additives in the polyelectrolyte solutions which may affect the thin film mechanical properties. Optionally, the polyelectrolyte solutions may comprise one or more "salts." A "salt" is defined as a soluble, ionic, inorganic compound that dissociates to stable ions (e.g., sodium chloride). A salt is included in the polyelectrolyte solutions to control the thickness of the adsorbed layers. More specifically, including a salt increases the thickness of the adsorbed polyelectrolyte layer. In general, increasing the salt concentration increases the thickness of the layer for a given spray coverage and contact time. This phenomenon is limited, however, by the fact that upon reaching a sufficient salt concentration, multilayers tend to dissociate. Typically, the amount of salt added to the polyelectrolyte solution is about 10% by weight or less.

Both dip coating and spraying permit a wide variety of additives to be incorporated into a film as it is formed. Additives that may be incorporated into polyelectrolyte multilayers include inorganic materials such as metallic oxide particles (e.g., silicon dioxide, aluminum oxide, titanium dioxide, iron oxide, zirconium oxide, and vanadium oxide) and clay minerals (e.g., hectorite, kaolin, laponite, montmorillonite, and attapulgite). For example, nanoparticles of zirconium oxide added to a polyelectrolyte solution or complex solution tend to improve the abrasion resistance of the deposited film. See Rosidian et al., *Ionic Self-assembly of Ultra Hard ZrO$_2$/polymernanocomposite Films*, Adv. Mater. 10, 1087-1091.

C. Methods of Deposition

The membranes for the preferred embodiments of this invention comprise multiple interactions which are responsible for holding these membranes together. The membranes may be deposited on surfaces by evaporation of solutions containing membrane materials, or, preferably, the membranes are deposited on a substrate by the alternating layer-by-layer thin film growth method. This method is known by those skilled in the art to yield uniform films (see *Multilayer Thin Films. Sequential Assembly of Nanocomposite Materials*, Decher and Schlenoff, Eds., Wiley-VCH, Weinheim, 2003) of reproducible composition.

For the embodiments of this invention employing polyelectrolyte complex thin films, a preferred method of depositing said complex is by the alternating layer-by-layer deposition method. The preferred concentration for solutions comprising polyelectrolytes to be deposited is in the range 0.01 weight % to 10 weight %, and preferably 0.1 weight % to 1 weight %. The alternating polyelectrolyte layering method, however, does not generally result in a layered morphology of the polymers with the film. Rather, the polymeric components interdiffuse and mix on a molecular level upon incorporation into the thin film. See Lösche et al., *Macromolecules* 31, 8893 (1998). Thus, the polymeric components form a true molecular blend, referred to as a "polyelectrolyte complex," with intimate contact between polymers driven by the multiple electrostatic complexation between positive and negative polymer segments. The complexed polyelectrolyte within the film has similar morphology as a polyelectrolyte complex formed by mixing solutions of positive and negative polyelectrolyte. It is also known that although there is extensive intermingling of neighboring layers over a range of 4-6 nominal layers, it is possible to obtain actual layers of different composition, or strata, by interspersing several layers made from one pair of polyelectrolytes by several layers made from a different pair. See Lösche et al., *Macromolecules* 31, 8893 (1998). For example, if polymers A and C are positively charged and polymers B and D are negatively charged, about 3 or 4 pairs of A/B layers followed by about 3 or 4 pairs of A/D or C/D layers will produce two strata of distinct composition.

Alternatively, the thin film coating may be applied to a surface using a pre-formed polyelectrolyte complex. See Michaels, *Polyelectrolyte Complexes*, Ind. Eng. Chem. 57, 32-40 (1965) and Michaels (U.S. Pat. No. 3,467,604). This is accomplished by mixing the oppositely-charged polyelectrolytes to form a polyelectrolyte complex precipitate which is then dissolved or re-suspended in a suitable solvent/liquid to form a polyelectrolyte complex solution/dispersion. The polyelectrolyte complex solution/dispersion is then applied to the substrate surface and the solvent/liquid is evaporated, leaving behind a film comprising the polyelectrolyte complex. To aid in dissolution or dispersion of the complex, both a salt, such as sodium bromide, and an organic solvent, such as acetone is added to the solution comprising the precipitated complex. It is known that the material obtained by layering two polyelectrolytes is substantially the same as material obtained by mixing and precipitating said polymers to form a polyelectrolyte complex.

In one embodiment of this invention, a polyelectrolyte complex is formed on a polymer or plastic surface. Polyelectrolyte complexes, especially those formed by the layer-by-layer alternating deposition technique, are known by those skilled in the art to adhere to plastic materials. For example, Chen and McCarthy (*Macromolecules*, 30, 78 (1997) describe the layer-by-layer deposition of polyelectrolyte complex on poly(ethylene terephthalate). Even fluorinated polymers, such as Dupont's Teflon™, are known to be coated by polyelectrolyte complex using the layer-by-layer technique (see Hsieh et al. *Macromolecules*, 30, 8453 (1997). Barker et al. (*Anal. Chem.*, 72, 5925 (2000)) and Locascio et al. (U.S. Pat. Pub. No. 2002/0053514) have disclosed the layer-by-layer deposition of polyelectrolytes on plastics. Thus, preferred substrates which may be formed and coated with polyelectrolyte complex include polycarbonate, poly (methyl methacrylate), polystyrene, poly(ethylene terephthalate), polysulfone, or polyamide. Since they are electrically insulating, it is preferred to coat plastics with a conductive film if the transport of species A is to be detected by electrochemical methods or ECL. Plastics not coated by a conductive layer are preferred for calorimetric or fluorescence quenching detection of the transport of species A across the MRIPM.

A preferred methods for coating the MRIPM on the inside surface of a channel or passage is to alternately pump solutions through the microchannel, said pumping achieved by pressure- or electroosmotic-driven flow.

For fast throughput and coating of surfaces, one method of applying the polyelectrolyte complex is by alternate spraying of a surface. Spraying is especially preferred when applying the coating to large areas using alternating exposure of oppositely-charged polyelectrolyte solutions. Spraying alternating oppositely-charged polyelectrolyte solutions has several advantages over the Michaels coating and evaporation method, including: improved control over film thickness especially the ability to make extremely thin films (e.g., less than about 1 μm), enhanced uniformity of film thickness especially over uneven surfaces and contours, and films may be produced without the use of organic solvents which may require precautions to avoid negative health and/or environmental consequences. The solutions may be sprayed onto a substrate by any applicable means (e.g., an atomizer, an aspirator, ultrasonic vapor generator, entrainment in compressed gas, or inkjet sprayer). In fact, a hand operated "plant mister" has been used to spray the polyelectrolyte solutions. Typically, the droplet size in the spray is about 10 nm to about 1 mm in diameter. Preferably, the droplet size is about 10 μm to 100 μm in diameter. The coverage of the spray is typically about 0.001 to 1 mL/cm$^2$, and preferably about 0.01 to 0.1 mL/cm$^2$.

The duration in which the polyelectrolyte solution is typically in contact with the surface it is sprayed upon (i.e., the contact time) varies from a couple of seconds to several minutes to achieve a maximum, or steady-state, thickness. The contact duration is selected based on the desired relationship between throughput (i.e., the rate at which alternating layers are created) and layer thickness. Specifically, decreasing the contact duration increases throughput and decreases layer thickness whereas increasing the duration decreases throughput and increases thickness. Preferably, the contact time is selected to maximize the throughput of layers that have a satisfactory thickness and are uniform across the surface.

Other preferred methods of depositing the polyelectrolyte solutions and/or polyelectrolyte complex include casting, dip coating, and doctor blading. Particularly preferred methods are dip coating and spraying.

Rinsing, to remove nonadsorbed polyelectrolyte, between the application of each polyelectrolyte solution is preferred. The rinsing liquid comprises an appropriate solvent (e.g., water or organic solvent such as alcohol). Preferably the solvent is water. If the solvent is inorganic (e.g., water), the rinsing liquid may also comprise an organic modifier (e.g., ethanol, methanol or propanol). The concentration of organic modifier can be as high as less than 100 percent by weight of the rinsing liquid, but is preferably less than about 50 percent by weight. The rinsing liquid may also comprise a salt (e.g., sodium chloride) which is soluble in the solvent and the organic modifier, if included in the rinsing liquid. The concentration of salt is preferably below about 10 percent by weight of the rinsing liquid. It should be noted that as the concentration of organic modifier increases the maximum solubility concentration of salt decreases. The rinsing liquid, however, should not comprise a polyelectrolyte. The rinsing step may be accomplished by any appropriate means (e.g., flushing, dipping, or spraying). Preferably, the rinsing step is accomplished by flushing. For spray rinsing, the amount of waste is preferably reduced by recycling the polymer solutions removed from the surface. Optionally, prior to depositing the second through n$^{th}$ layer of sprayed oppositely charged polyelectrolyte solution, the surface of the multilayer structure may be dried.

Particles with diameters ranging from nanometers to millimeters may also be coated with polyelectrolyte complex. If the alternate layering method is used, it is not practical to coat particles individually. Neither is the spray method practical, unless particles are larger than about 100 μm. Instead, batches of particles are alternately immersed in coating solutions, with intervening rinse, as detailed by Caruso and Sukhorukov, Chapter 12 in *Multilayer Thin Films*, G. Decher and J. B. Schlenoff, Eds., Wiley-VCH, Weinheim, 2003. See also Donath et al. U.S. Pat. Pub. No. 2003/0219384. Optionally, after coating with MRIPM, particles may be degraded to yield hollow capsules.

In yet another embodiment of the present invention the polyelectrolyte complex is a coating or layer on a substrate or substratum and may be deposited according to any appropriate method (see, e.g., supra, as a multilayer or as a pre-formed polyelectrolyte complex). The substratum may be non-porous or porous and may be comprised of many types of materials that are well known in the art such as polymers, metals, and ceramics. The surface of polymeric support materials may be positively charged by comprising tetraalkyl ammonium groups, negatively charged by comprising sulfonate groups, or neutral. In another embodiment the substratum is porous and comprises a material selected from the group consisting of polypropylene, nylon, polytetrafluoroethylene, glass, and alumina (all of which are known to those of skill in the art). Typically, the average size of the pores is between about 100 nm and about 10 μm, and the degree of porosity is between about 0.1 and about 60%.

While the embodiments detailed above have focused on a membrane on the surface of, and in contact with a substrate, in other embodiments there is no substrate. Thus, in other embodiments of this invention the membrane is curved and forms a capsule. Such a capsule is known by those skilled in the art (see Möhwald et al. Chapter 13 in *Multilayer Thin Films. Sequential Assembly of Nanocomposite Materials*, Decher and Schlenoff, Eds., Wiley-VCH, Weinheim, 2003) to be between 10 nm and 100 micrometers and is, more preferably, in the range 100 nanometer to 10,000 nanometers. In one embodiment, species A resides inside the capsule and species B is provided outside the capsule and acts to release species A from the capsule. In another embodiment, species A is outside the capsule and is loaded into the capsule under the influence of species B, which makes the capsule more permeable.

The following nomenclature for multilayers is used to describe MRIPMs: $(P/Q)_x$ where P is the starting polyelectrolyte contacting the substrate, Q is the terminating polyelectrolyte in contact with subsequent protein solutions and x is the number of layer pairs. In $(P/Q)_x P$, P would be the terminating polymer. Salt, MY (cation M and anion Y), has an important role in the buildup process and is represented by $(P/Q)_x$ @c MY, where c is the molarity of the salt (MY) in the polymer solution. The pH can be included in the nomenclature when using pH dependent MRIPMs. For example, (PAH/PAA)$_2$PAH @0.25M NaCl @pH 7.4, represents two layers pairs of PAH/PAA, terminated with a layer of PAH, built at 0.25 M NaCl and a pH of 7.4.

The following examples further illustrate the present invention. The above described polyelectrolytes, additives, and deposition methods were used for building MRIPMs of a variety of compositions on substrates. The MRIPMs, solutions, and additives were modified in various ways as shown in the examples, and the effects of those modifications on the ability of the MRIPM to control the transport of species through the MRIPM and detection thereof were monitored.

Example 1

Doping a Polyelectrolyte Complex Film with Specific Interacting Species B

Poly(styrenesulfonic acid), PSS (molar mass ~70,000) and poly(diallyldimethylammonium chloride), PDADMAC (molar mass ~3-4×10⁵), purchased from Aldrich, were dialyzed against distilled water using 3,500 molar-mass-cutoff dialysis tubing (Spectra/Por). Sodium chloride (Fisher), potassium ferrocyamide (Fisher), potassium ferricyanide (Mallinckrodt) and potassium hexacyanocobaltate (Aldrich) were used as received.

Figure 3:
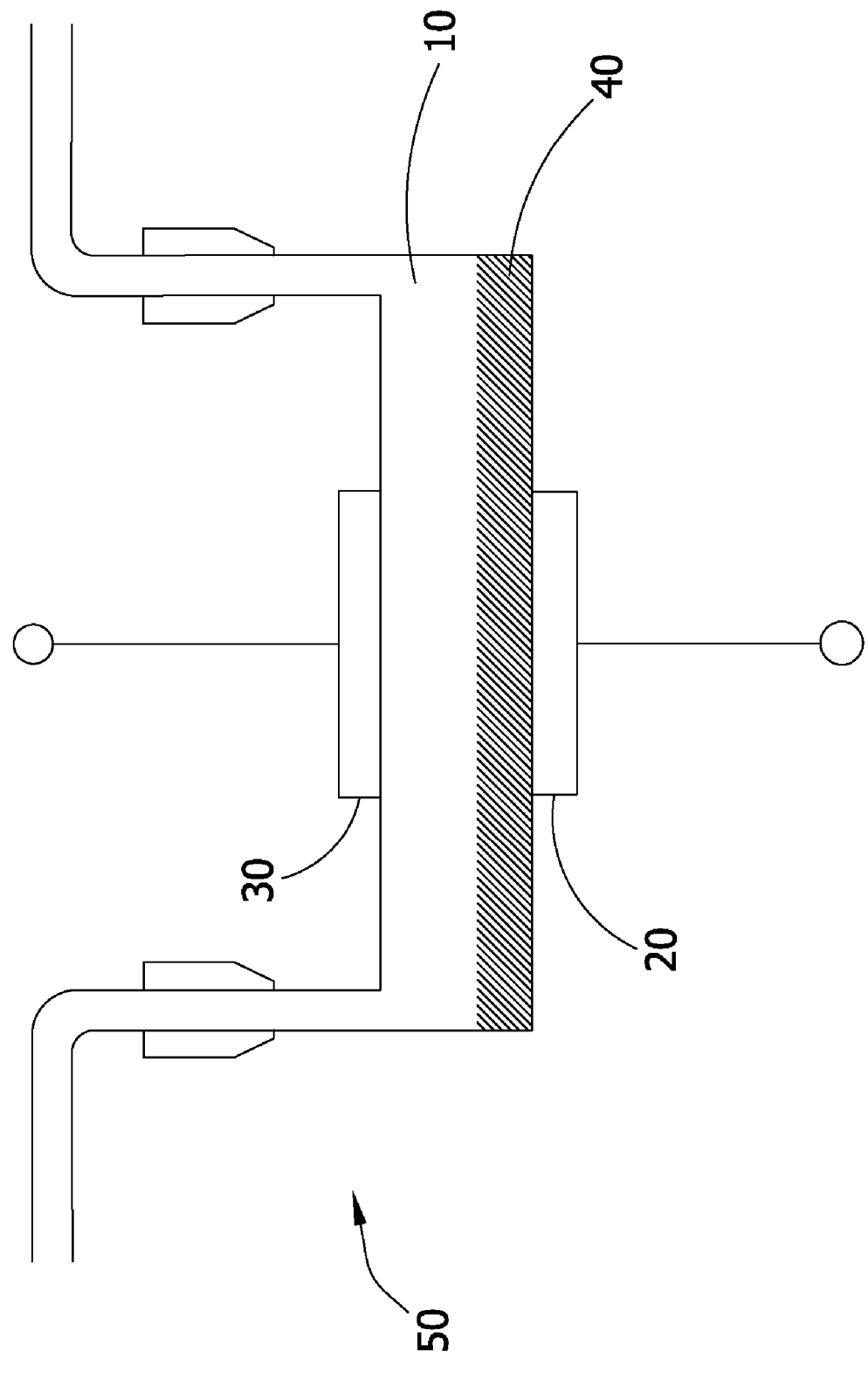
FIG. 3 shows a MRIPM acting as a "transistor" according to the method of Example 1. Two electrodes, one electrode 20 coated with a polyelectrolyte multilayer MRIPM 40, and the other electrode 30 bare, are separated by a channel 10 containing a constant concentration of redox-active species A and a variable concentration of species B. An electrochemical current flowing in the forward, $i_f$ direction, is carried through the multilayer by ferricyanide ions, whereas in the reverse direction it is carried by ferrocyanide ions. The multilayer is comprised of a complex of poly(diallyldimethylammonium) and poly(styrene sulfonate).

Electrochemical measurements were made using the flow cell 50 depicted in FIG. 3. The flow cell consisted of two plastic plates, 40 mm×20 mm×10 mm, separated by a 0.5 mm rubber gasket, each with a 2 mm diameter platinum electrode. Potential was controlled by a Princeton Applied Research 273 potentiostat, in the two-electrode configuration, interfaced to a PC.

One of the electrode surfaces was coated with a polyelectrolyte multilayer. To prepare the electrode surface for multilayer deposition it was polished with 0.05 μm alumina (Buehler), sonicated, and rinsed in water. Sequential adsorption of polyelectrolytes onto the cell block was performed with the aid of a robot (StratoSequence V, nanoStrata Inc.). The two polymer deposition solutions contained $10^{-2}$ M PSS or $10^{-2}$ M PDADMAC, both in 0.25M NaCl. Between alternate exposures to the polyelectrolytes, there were three rinses of fresh distilled water. Rinse and polymer solution volumes were approximately 50 mL each. The deposition time for each layer was 5 min and the rinse time 1 min. The last (PSS) layer (20$^{th}$ layer) was deposited from solution containing 10 mM salt. Film thickness, measured with an ellipsometer, was 83 nm.

Synthesis of the device shown in FIG. 3 is extremely facile, benefiting from the simplicity of the layer-by-layer approach of assembling multicomposites. The plate 20 bearing the "emitter" electrode was dipped in aqueous solutions of polyelectrolytes in an alternating manner, with rinse in pure water between layers. Each dip deposits a uniform layer of polymer and reverses the surface charge. Individual polyelectrolyte "layers" interpenetrate forming rugged electrostatic, or ion-pairing, bonds. In this manner, the emitter electrode 20 was coated with a polyelectrolyte multilayer MRIPM 40. The other plate bearing an electrode 30 was left bare.

All measurements were performed at room temperature using 1 mM ferricyanide/1 mM ferrocyanide solutions as polyvalent species A, with different salt concentrations, which were fed through the flow cell by gravity at 25 mL/min. Salt was either sodium chloride or potassium hexacyanocobaltate. In this example, sodium and chloride ions in salt solutions were examples of nonselective species B, known to those skilled in the art (e.g. see Farhat and Schlenoff, Langmuir, 17, 1184 (2001)), and hexacyanocobaltate ion was an example of polyvalent selectively interacting species B. In separate experiments it was found that the membrane distribution coefficient (K) for hexacyanocobaltate was approximately 70. In other words, the membrane concentration, at equilibrium, of hexacyanocobaltate was 70 times the solution concentration.

Figure 4:
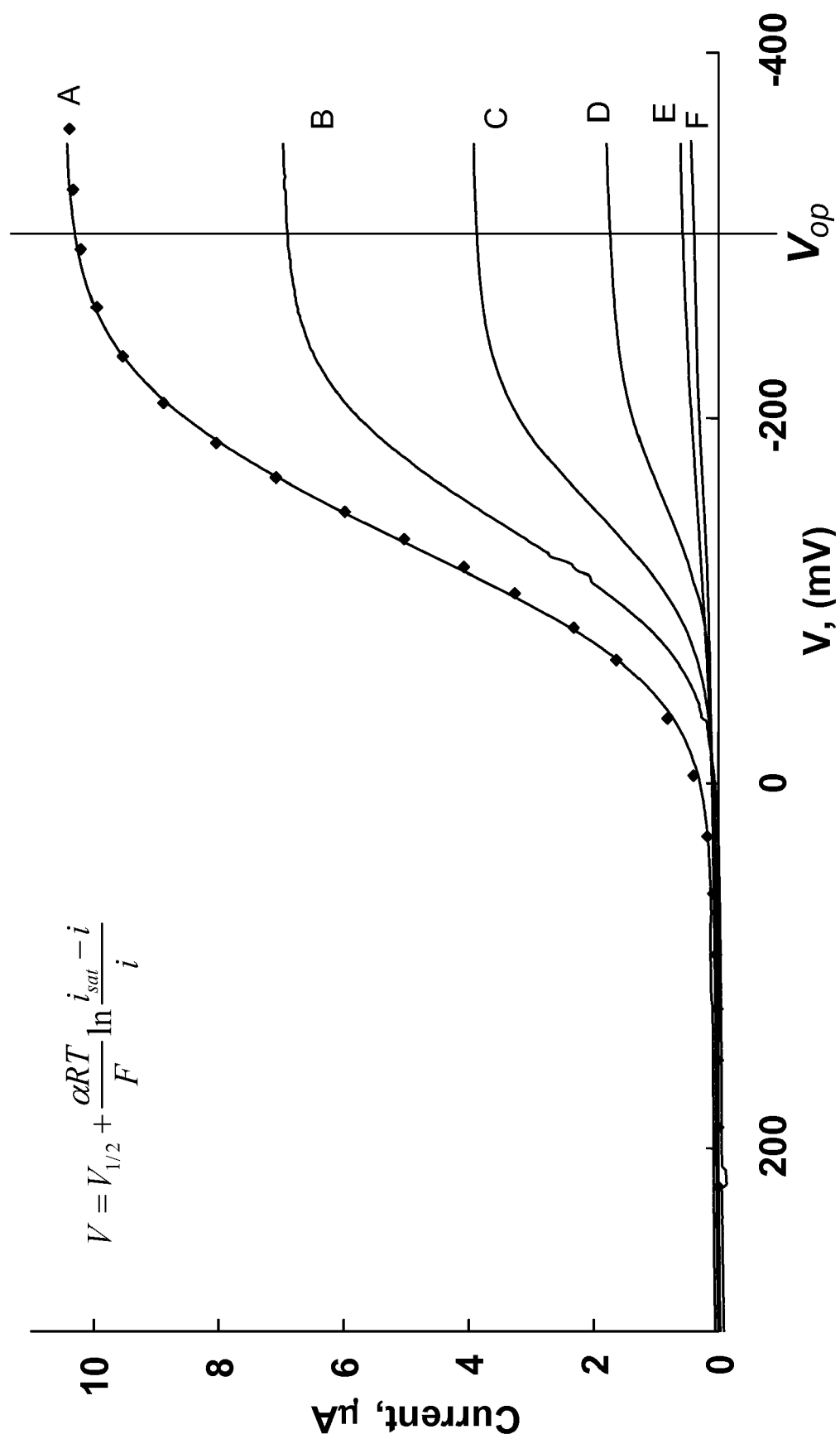
FIG. 4 is a family of i/V curves using the device shown in FIG. 3 and developed according to the method of Example 1. Current flows through the multilayer according to the equation shown, where $i_{sat}$ is the saturation current, $V_{1/2}$ is the half-wave potential, R is the gas constant, T is the temperature, F is Faraday's constant, and $\alpha$ is a shape factor between 1 and 2. Increasing concentrations of salt (f→a, (F) 0.1, (E) 0.2, (D) 0.4, (C) 0.6, (B) 0.8, (A) 1.0 M) lead to higher doping of the multilayer, which produces more sites for ion transport. The concentration of ferri-(ferro)cyanide probe ions (species A) was constant ($10^{-3}$M).

Electrolyte was passed through the channel 10 between the multilayer-bearing electrode 20 and the opposing bare electrode 30, as shown in FIG. 3. This is a two-electrode device, which, compared to the three-electrode configuration, simplifies the detection electronics and eliminates the requirement for a separate reference electrode. Current was monitored as a function of voltage applied (FIG. 4). The electrochemical reactions corresponding to forward, $i_f$, and reversed, $i_r$, bias are shown as follows:

a:

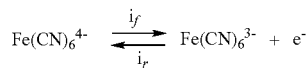

b:

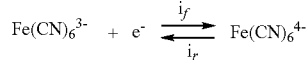

In the forward direction, electrochemical current is transported through MRIPM membrane, 40, by ferricyanide (−3 charge) and in the reversed direction by ferrocyanide (−4 charge). Since the latter is more highly charged it moves through the multilayer much more slowly and virtually no reversed bias current is observed. The device shows "transistor-like" properties, such as rectification (FIG. 4), and current is a nonlinear function of voltage up to a saturation plateau, which represents the diffusion-limited rate of ion transport.

Another transistor-like feature is "gating" by added salt. Salt dopes the multilayer, rendering it more conductive via the mechanism summarized above. The resulting family of current/voltage curves is displayed in FIG. 4. The shape of the wave is modeled assuming current to be limited by diffusive mass transport through a thin film i.e. driven by concentration gradients (chemical potential) and not by electric fields. The equation for this theoretical response is presented on FIG. 4.

Figure 5:
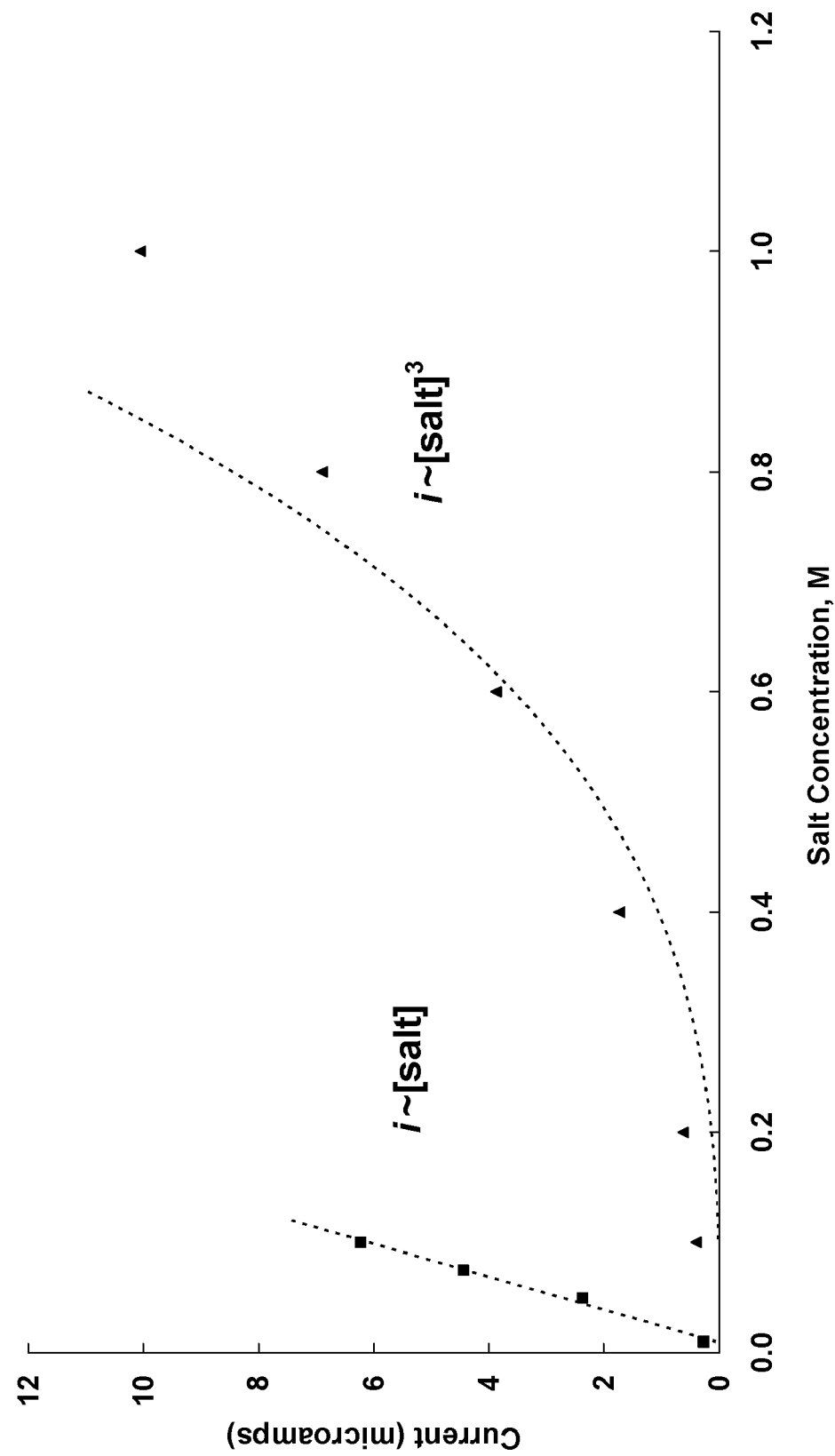
FIG. 5 shows the response of $i_{sat}$ to Species B concentration for the device shown in FIG. 3 and developed according to the method of Example 1. When species B is (nonselective) NaCl (▲), the current is much lower, than when the species is (selective) colbalticyanide (■).

A common mode of employing a transistor is to maintain voltage at the saturated current regime and vary the gate potential, $V_g$. The (typically linear) i/V response is used for electronic amplification. FIG. 5 depicts current vs. salt concentration for $V_{applied}$ at a point ($V_{op}$) chosen to be on the current plateau region in FIG. 4. The nonlinear response of current to NaCl concentration for a constant ferricyanide ($Fe(CN)_6^{3-}$) probe ion concentration (i~[NaCl]³) is evident (FIG. 5). Negative deviation from the predicted power law at high [NaCl] is due to the series resistance of the stagnant layer of solution next to the electrodes, which becomes significant as the membrane resistivity decreases (current for bare electrode 30 was 22 μA).

A selective species B, especially a polyvalent charged dopant, having particular chemical affinity with the membrane will enhance doping, as in Eq. 1, inducing significant permeability. This preferred feature of the invention is illustrated by the use of cobaltocyanide ($Co(CN)_6^{3-}$) as the anion rather than Cl⁻. Cobaltocyanide itself is electrochemically inert and thus not observed by the experiment (does not contribute to electron current observed in the external circuit). However, using triple-charged cobaltocyanide as the selective species B illustrates how the current of species A through the MRIPM is enhanced compared to the current using unselective NaCl as species B (FIG. 5).

Figure 6:
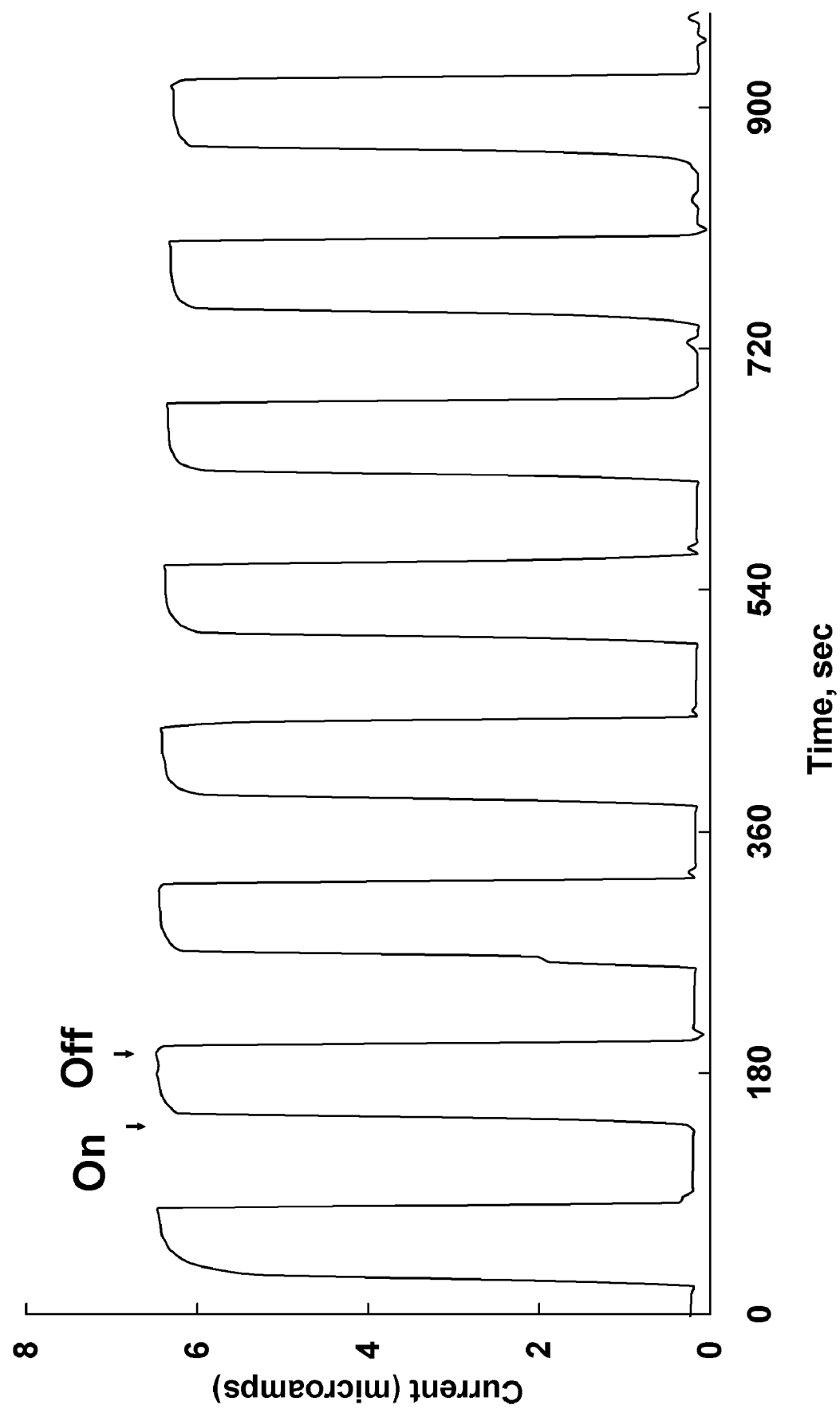
FIG. 6 shows switching of the permeability of the MRIPM under the influence of species B. According to the method of Example 1, the device from FIG. 3 is exposed alternately to high (0.8 M) and low (0.01 M) concentrations of salt. Response is reversible, but the switching time is slow (about 8 sec for "on" and about 5 sec for "off").

Continuing the parallels with semiconductor transistors, switching of the device in FIG. 3 is accomplished by poising the voltage at $V_{op}$ and alternating between high and low salt gate concentrations, as in FIG. 6. The resistance in the "on" state (0.8 M salt) and the "off" state (0.01 M salt) differs by a factor of 30. Although FIG. 6 clearly shows good reversibility, it also demonstrates a relatively slow switching time, due to the requirement for physical diffusion of salt ions into/from the multilayer. The salt gated device will not compete for speed with semiconductor based electron transport devices. Rather, it should be considered an alternative modality of direct chemical amplification or signal transduction.

Example 2

Detecting the Passage of Species a Across a MRIPM with Electrochemically Generated Chemiluminescence (ECL)

PEMUs comprising 10 layers of PSS and 10 layers of PDADMA were built on a platinum electrode in 0.1M phosphate buffer, pH 7.2, in 0.2M NaCl. Anionic and cationic polyelectrolyte solutions were both 1 mM (based on the polyelectrolyte repeat unit). During construction, the PEMU was rinsed in aqueous solution of the above mentioned salts only, for 1 minute, in between polyelectrolyte dips. Twenty layers were built in this manner on each electrode used in the experiment. The MRIPM was about 70 nm thick.

PEMUs MRIPMs were annealed for 48 hours in 1 M NaCl before ECL readings were made. ECL was recorded while cycling the potential from 0.6 to 1.4V, at 6V/min, with a Ag/AgCl reference electrode because that is the range where the ECL reagents undergo redox reactions and luminesce the most. The potentiostat used was a Pine Instrument Bipotentiostat. The electrochemical cell contained a solution of $10^{-5}$ M Ru(bipyridine)$_3$Cl$_2$ (RuBipy), 0.1 M phosphate buffer, pH 7.2 and 0.05M tripropylamine, in addition to NaCl added at specified concentrations.

The luminescence was recorded with a R3823 Hamamatsu photomultiplier tube (PMT), biased to 954V by a Bertan 313B High Voltage power supply. Current readings from the PMT were recorded with a Keithley 617 Programable Electrometer and fed into a Pentium III computer with a Labview interfacing program. Experiments were conducted in a home made dark box, with dark currents between 1 and 1.5 nA. In this experiment, species A is RuBipy and species B is nonselective, (NaCl).

Figure 7A:
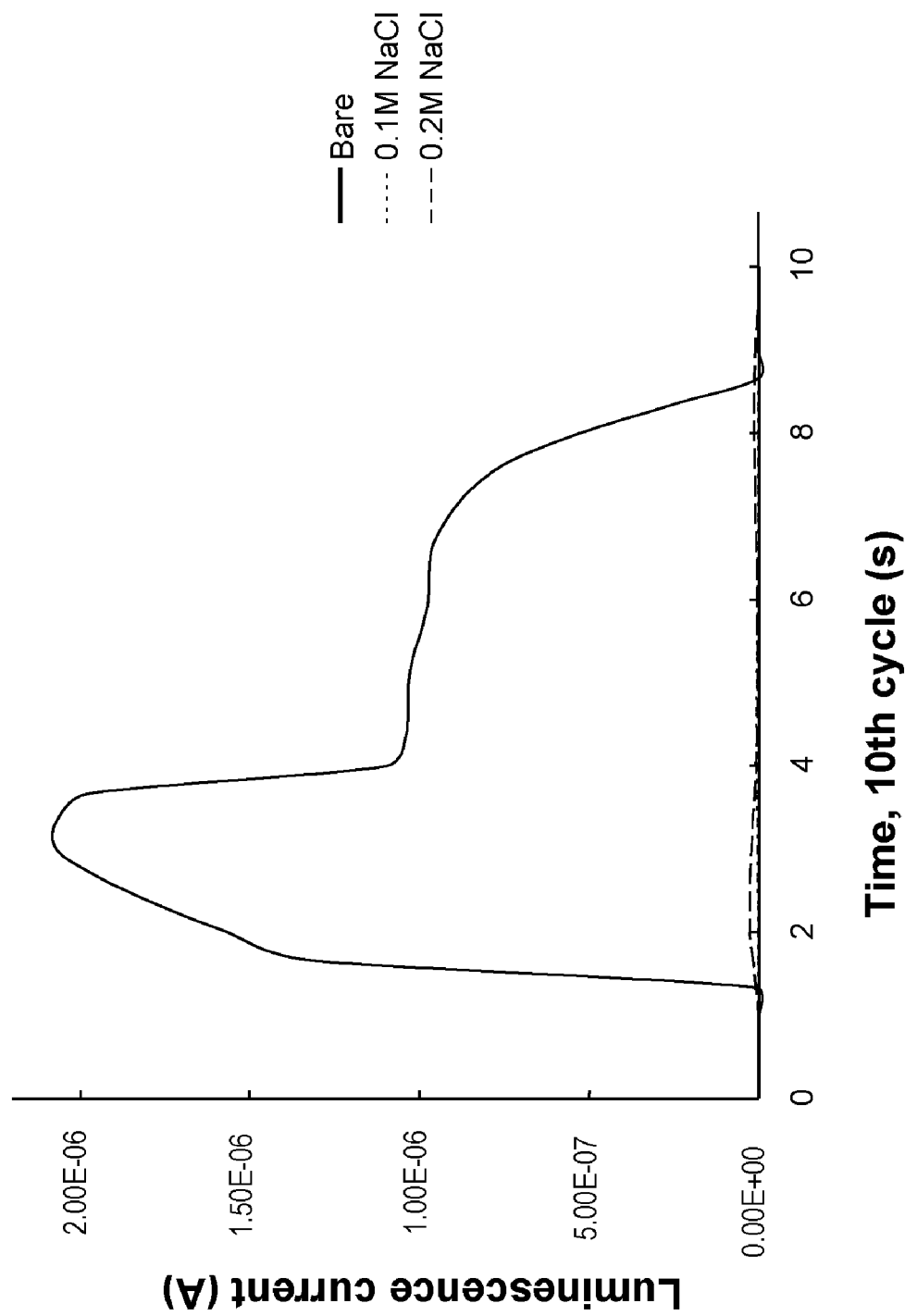
FIGS. 7A and 7B show electrogenerated chemiluminescence at an electrode coated with a MRIPM, according to the method of Example 2. The MRIPM is a PEMU comprising 10 layers of PSS and 10 layers of PDADMA, alternately deposited, on a platinum electrode in 0.1 M phosphate buffer, pH=7.2 in 0.2 M NaCl. This electrode was immersed in 0.00001 M ruthenium bipyridine in 0.1 M phosphate buffer, pH 7.2 and 0.05 M tripropylamine, together with specified NaCl concentration. The voltage was scanned, at 100 mV per second, from 0.6 V to 1.4 V and back. The light collected with a PMT during this scan produced a luminescence current, which is presented as a function of time. The light output of the bare electrode (solid line of 7A) is much greater than the MRIPM-covered electrode immersed in solution with 0.1 M salt (dotted line of 7B) or 0.2 M salt (dashed line of 7B) added. The peak current in 0.2 M NaCl is significantly greater than the response in 0.1 M NaCl, demonstrating the effect of species B (salt) at moderating the MRIPM transport of species A (ruthenium bipyridine).
Figure 7B:
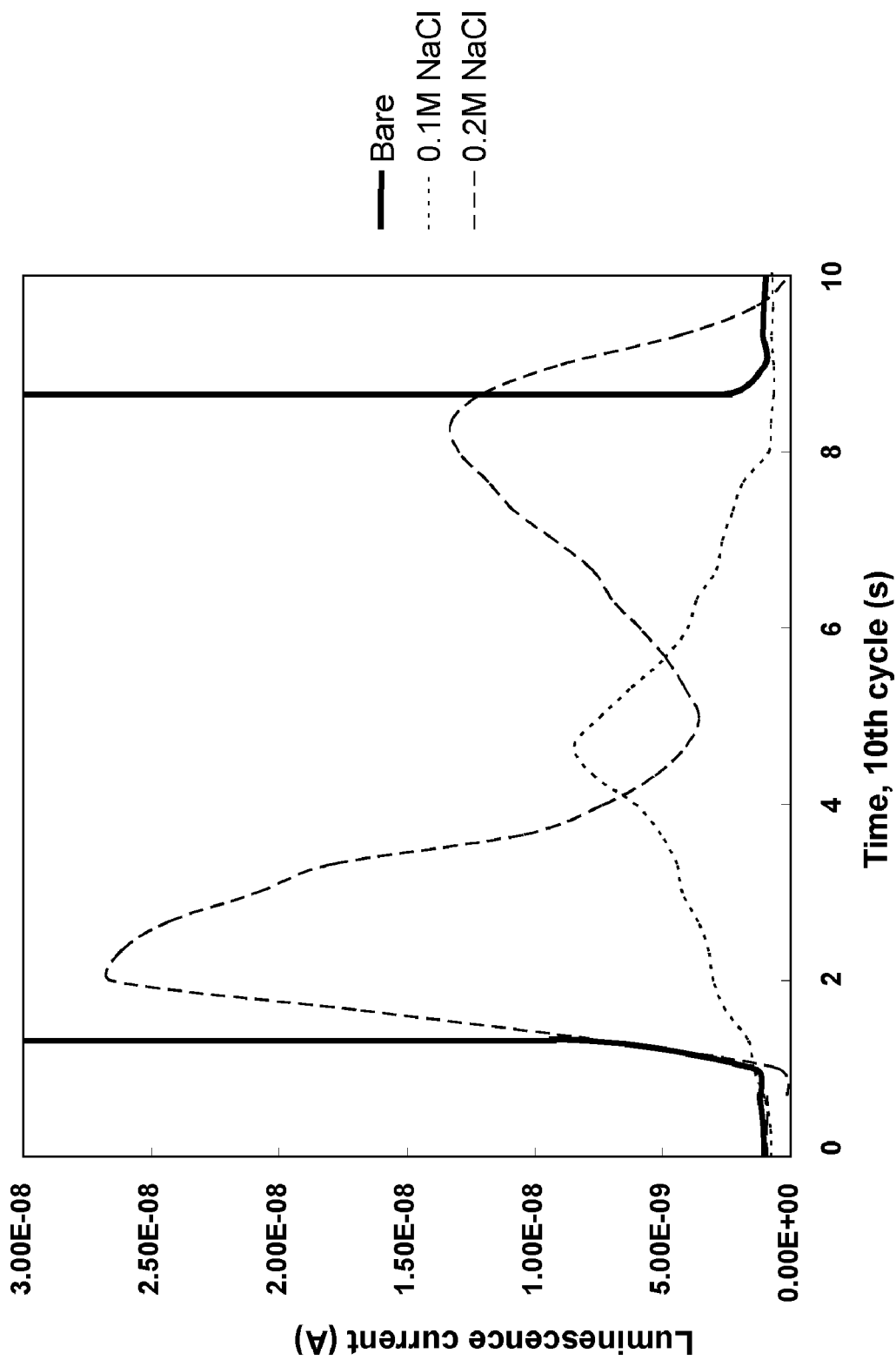

The time course in FIGS. 7A and 7B from 1 sec to 9 seconds represents one voltage scan from 0.6 to 1.4 volts and back to 0.6 V. As seen in FIG. 7A, the ECL signal for the bare electrode is much greater than that for the PEMU coated electrode, reflecting the ability of the PEMU to block RuBipy. FIG. 7B is a magnified current scale. The maximum ECL intensity recorded by the PMT is at approximately 1.2V. Although the positions of the peaks are not the same, it is clear that the membrane is more permeable to RuBipy in higher concentrations of NaCl, since the ECL intensity is greater.

Example 3

Preparing MRIPM Membranes with Continuously Variable Composition

Silicon wafers (Si<100>, 0.5 mm thick, 1 in. diameter, undoped, double-side polished from Topsil Inc.) were cleaned in "piranha" solution (70% $H_2SO_4$ (conc.)/30% $H_2O_{2(aq)}$) and then in $H_2O_2$/ammonia/water 1:1:7 vol/vol, rinsed in distilled water and dried with a stream of $N_2$.

To prepare multilayers on these Si wafers they were affixed to a stainless steel shaft with Teflon™ tape. The shaft was rotated at 300 rpm by a small DC motor. A robotic platform (StratoSequence V, nanoStrata Inc.), accommodating eight 100 mL beakers, was programmed to expose the wafer alternately to the 1 mM polymer solutions, with acidic water rinses in between. The salt concentration (NaCl) in the deposition solutions was 1.0 M. The pH of both deposition solutions and rinsing water were adjusted to 2 by HCl.

Transmission IR spectra were recorded with a Nicolet Avatar 360 FTIR spectrometer. The thickness of the dried multilayers was measured with a Gaertner Scientific L116S ellipsometer, using 632.8 nm light at 700 incidence angle. A refractive index of 1.55 was employed for multilayers. Atomic force microcopy, AFM (Dimension 3100, Digital Instruments) in Tapping Mode™ was used to track the multilayer surface morphology change.

ATR measurements were performed with a Nicolet Nexus 470 fitted with a 0.5 mL capacity flow-through ATR assembly (Specac Benchmark) using a 70×10×6 mm 45° germanium crystal. Each spectrum had 32 scans coadded at a resolution of 4 cm$^{-1}$. Multilayers were deposited on the ATR crystal while it was loaded in the flow cell by passing polyelectrolyte and rinse solutions, in an alternating manner, through the cell.

MRIPMs here are thin films of polyelectrolyte complexes, made by the multilayering technique, using poly(styrene sulfonate), PSS, as a permanently charged negative polyelectrolyte, and a mixture of poly(diallyldimethylammonium chloride), PDADMA, and a random copolymer of diallyldimethylammonium and acrylic acid, PDADMA-co-PAA, (0.64/0.36 mole ratio of respective monomer units, rendering the copolymer net positive at all pH). Coatings were prepared in buffers at low pH with the last layer the copolymer (positive) having the carboxylic acid groups in the protonated (neutral) state. The copolymer is commercially available (Merquat®, Calgon Inc.) as an ingredient for personal care products. The carboxylates on the Merquat® were "diluted" by adding pure homopolymer PDADMA to the "polycation" solution. Since the concentration of PAA in the pure Merquat® polymer is 36 mol %, the final nominal concentration of carboxylates in the multilayer, expressed as a molar ratio or mole % of total PAA+PDADMA units, is given by $$PEMU mol\% PAA = \frac{[Merquat\circledR]}{[Merquat\circledR] + [PDADMA]} \times 36$$

Since in this work a mixture of copolymer PDADMA-co-PAA and homopolymer PDADMA was used in the "cationic polyelectrolyte" solution for the PEMU buildup, the term for this polycation mixture is defined as copolymer-blend-PDADMA. The subscript "Φ" describes the mole fraction of copolymer in the cationic buildup solutions. For example, (copolymer$_{0.2}$-blend-PDADMA$_{0.8}$/PSS)$_{10}$ @1.0M NaCl @pH 2, represents ten bilayers made from a solution 20 mol % PDADMA-co-PAA copolymer and 80 mol % PDADMA homopolymer, and a solution of PSS, built at 1.0 M NaCl and a pH of 2.

Figure 8:
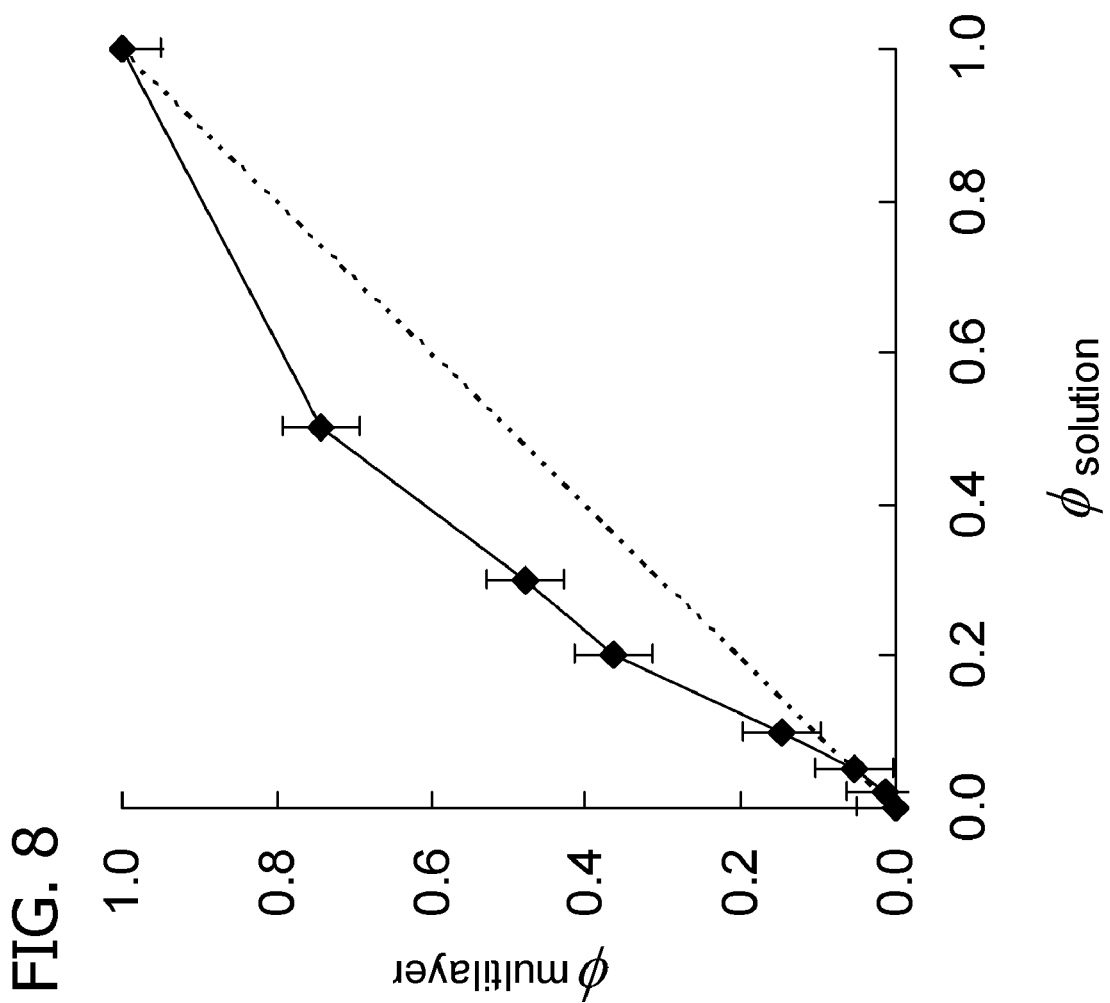
FIG. 8 shows mole fraction of the copolymer PDADMA-co-PAA in the multilayer ($\Phi_{multilayer}$) vs. mole fraction in the polycation solution ($\Phi_{solution}$), according to the method of Example 3. (copolymer$_\Phi$-blend-PDADMA$_{1-\Phi}$/PSS)$_{10}$ @1.0M NaCl @pH 2 was deposited on the silicon wafer. The dotted line shows "ideal" multilayer blend formation, for the case where the mole faction in the PEMU is the same as the mole fraction in solution.
Figure 9:
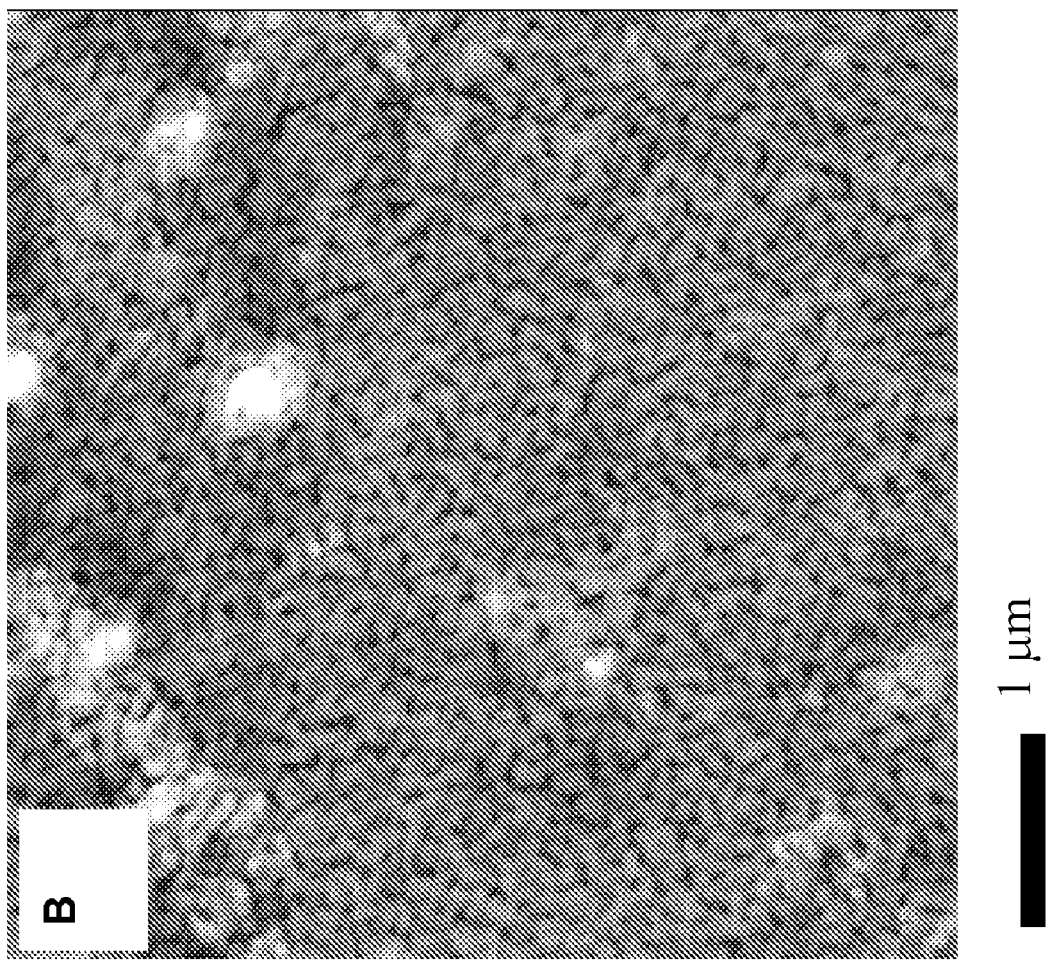
FIG. 9 is an AFM image of an 11-layer (copolymer$_{0.2}$-blend-PDADMA$_{0.8}$/PSS)$_5$copolymer$_{0.2}$-blend-PDADMA$_{0.8}$ @1.0M NaCl @pH 2, according to the method of Example 3.

Using FTIR of comparison samples on silicon wafers, it was verified that the multilayer carboxylate composition approximately reflects the solution composition from which the films are deposited. Ideally, the PAA component would be incorporated into the multilayer in the same proportion as copolymer in the mixed polycation solution. To ascertain whether this was, indeed, the case, the amount of copolymer in the multilayer was evaluated by transmission FTIR. Mole fractions of copolymer in the PEMU are plotted as a function of mole fraction in the polycation solution (FIG. 8). In the ideal case there would be no preference for either copolymer or homopolymer PDADMA, giving a slope of 1.0 (dotted line). A positive deviation indicates some preference for copolymer. Notwithstanding the slight preference for homopolymer, it is shown that PEMUs of continuously variable composition may be assembled by the blending strategy described. An Atomic Force Microscopy (AFM) micrograph of the surface of an 11-layer PEMU is shown in FIG. 9. This film is smooth and stable.

Example 4

Controlled Protein Adsorption on MRIPM Comprising Polyelectrolytes

FTIR (Nicolet Nexus 470 FTIR) was used in attenuated total internal reflection mode (ATR, Specac Inc., flow cell of volume 0.49 mL) to monitor protein adsorption onto polyelectrolyte multilayers assembled on an ATR cell housing a 70 mm×10 mm×6 mm 45° germanium (Ge) crystal. Multilayer buildup was done by alternately filling the ATR cell with polymers (1 mM in 0.25 M NaCl), with intervening rinses in water. Solution pH for buildup, including rinse, with PAH was stabilized with TRIS buffer (pH 7.4). The exposure time for each solution was 10 minutes. Multilayers for ATR were not dried before protein adsorption. A multilayer spectral background in buffer was taken prior to protein adsorption. Layer-by-layer buildup and protein adsorption were monitored using areas of characteristic bands of interest (sulfonate stretch for PSS, $\nu(SO_3)$, at ~1033 $cm^{-1}$ and amide II band at ~1540 $cm^{-1}$). All spectra were recorded using 32 scans and 4 $cm^{-1}$ resolution. After addition of protein solution to the ATR cell, the protein spectrum was monitored with time until there were no further significant changes in spectra, the cell was rinsed with buffer, and amide II peaks were integrated. $H_2O$ spectra were subtracted from raw infrared spectra. The amounts of proteins were calculated based on calibration curves for each protein.

UV-vis absorption spectra were recorded on quartz-supported multilayers using a Perkin Elmer UV/VIS/NIR spectrometer (Lambda 900). Fused quartz plates (2 mm thick, 1 inch diameter, GM Associates) were pretreated with "piranha" and then in $H_2O_2$/ammonia/water (1:1:7) then rinsed. Film thickness was estimated from multilayers deposited on the native $SiO_2$ layer (about 20 Å thick) on silicon wafers using the same conditions.

One of the objectives of the present invention is to create a protein-repelling multilayer comprising PAA, with the PAA limited to the surface. A composition gradient would be desirable where PEMU durability is an issue, since hydrophobic polyelectrolytes form less swollen and more resilient films. Thus, multilayers having a composition gradient, and therefore a hydrophilicity gradient, were prepared starting with PM2VP/PSS (relatively hydrophobic) and ending with PAA (relatively hydrophilic). Advantageously, one would preserve durability, but maintain surface repellency, with the hydrophilic polyelectrolyte limited to the outer, or outer few, layers. Also, using a specialized polymer as the outer layer only would help conserve a potentially costly material. Fibrinogen was used in this example since it is relatively large and is a model for "sticky" serum proteins (e.g. see Mrksich et al. *Langmuir*, 11, 4383 (1995)).

Table V shows that a PEMU with a hydrophobic bulk (PM2VP/PSS), capped with a hydrophilic surface (PAH/PAA), shows no significant change in fibrinogen adsorption compared to a PEMU of uniform hydrophilic composition (PAH/PAA). A surface layer is thus able to "mask" protein adsorption properties of bulk PEMU material. Another polymer known to those skilled in the art for its effectiveness in preventing protein adsorption is poly(ethylene oxide), PEO, also known as poly(ethylene glycol), PEG (e.g. see Harris, *Poly(ethylene glycol) Chemistry: Biotechnical and Biomedical Applications*, Plenum Press, New York, 1992). The ability of hydrophilic repeat units to reduce protein adsorption was also seen in other experiments comparing protein adsorption on PEMUs made from PM2VP-block-PEO and PSS, with those made from PM2VP and PSS and capped with one layer of PM2VP-block-PEO. The economical use of one layer only of diblock copolymer proved as effective as making the entire PEMU from the diblock.

TABLE V

Hydrophilicity/hydrophobicity gradient for fibrinogen adsorption

| Multilayer | Surface Charge | $\Gamma$, mg/m$^2$ |
|---|---|---|
| (PAH/PAA)$_3$ | — | $0.34 \pm 0.1^a$ |
| (PM2VP/PSS/PM2VP) (PAA/PAH/PAA) | — | $0.41 \pm 0.1^a$ |
| (PM2VP/PSS)$_3$ | — | $3.4 \pm 0.5^a$ |

$^a$Measured with ATR-FTIR

All proteins are rather "sticky", i.e., capable of adsorbing via electrostatic (including "patch charge" type adsorption), hydrogen bonding and "hydrophobic" interactions. Surfaces of opposite charge to that of the protein were found to be more effective at promoting protein adsorption. Where such electrostatic interaction dominates, increased ionic strength was shown generally to decrease protein adsorption. Also evident was the partial effectiveness of a hydrophilic neutral block (PEO) at preventing access to the charged surface beneath it. Protein adsorption was found to be enhanced at multilayers with opposite charge. In fact, the thickness of the PEMU was shown to play an important role in the adsorption process, since the PEMU can act as a "sponge" or a matrix to load proteins. Direct ATR-FTIR measurement on thicker PEMUs confirmed protein penetration into the multilayer matrix for oppositely charged surfaces, whereas AFM revealed islands of surface aggregate for like-charged multilayers. On exposure to solution of higher ionic strength, sorbed protein could be released by an ion exchange type mechanism.

Example 5

MRIPMs Comprising Polyelectrolytes Comprising Zwitterionic Groups

Zwitterionic Polyelectrolytes Comprise Repeat units that bear a negative and a positive charge. Opposite charges on a repeat unit are in relatively close proximity and therefore have an opportunity to interact strongly. Because the zwitterion group is charge balanced (charge neutral) it does not require counterions when in solution.

Given that opposite charges on zwitterion polymer repeat units interact with each other, the question arises as to whether polyzwitterions would interact with other charged polymers. If there is no electrostatic or charge-pairing interaction between molecules, there is no driving force for intermolecular attraction and therefore no driving force for polyelectrolyte complexation, which is required for multilayer buildup.

An attempt was made to construct a multilayer from the zwitterionic polymer poly(N-propane sulfonate-2-vinyl pyridine), P2PSVP, and a negative or positive polyelectrolyte. For example, P2PSVP and PDADMA were employed for attempted multilayer buildup at pH 5. Under this condition, the multilayer did not build because the negative sulfonate on the P2PSVP interacted with the positive pyridinium on P2PSVP, an intramolecular interaction, rather than with the PDADMA repeat unit (an intermolecular interaction). Similarly, multilayers could not be constructed from P2PSVP and PSS at near-neutral (pH 5-7) conditions because the PSS does not interact sufficiently with the pyridinium nitrogen on P2PSVP. However, if the pH is lowered below about pH 2, multilayers may be built from PSS and P2PSVP. This is because at this low pH even the strongly acidic sulfonate groups on P2PSVP are protonated, leaving some of the pyridinium groups unpaired for intermolecular interactions. Multilayers constructed in this way and exposed to higher pH developed porosity and decomposed as a result of the changing internal charge within the multilayer.

Figure 10:
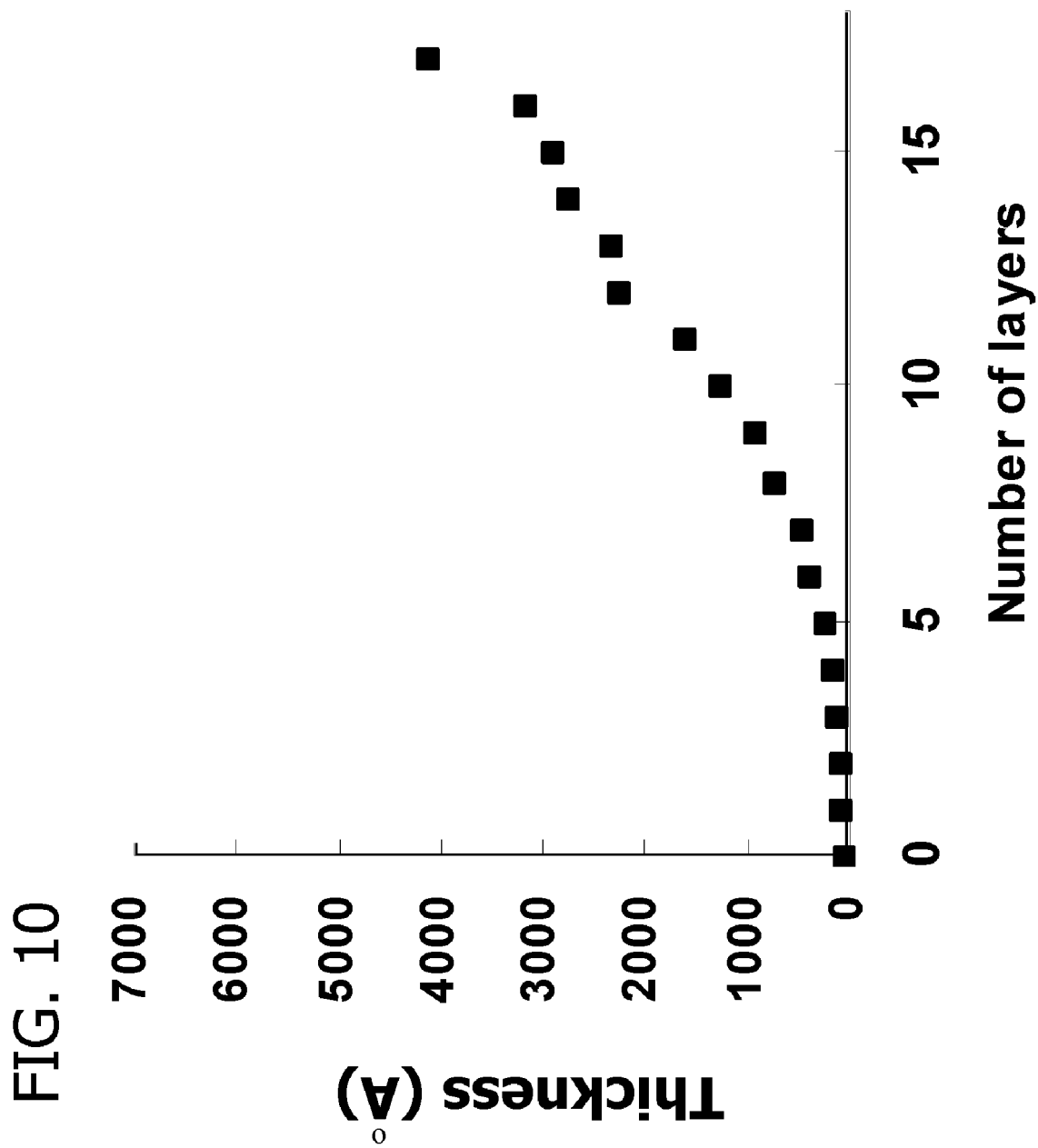
FIG. 10 shows ellipsometric data for thickness vs. number of layers for the buildup of poly(acrylic acid)-co-poly(3-[2-(acrylamido)-ethyldimethyl ammonio] propane sulfonate), PAA-co-PAEDAPS, and PAH on a silicon wafer, according to the method of Example 5.

In another example, PAA, PDADMA and P2PSVP were employed to make a multilayer. ATR-FTIR was used to check for layer-by-layer buildup. Although ellipsometry data showed that a film grows, ATR-FTIR revealed that PDADMA displaced any P2PSVP that had weakly adsorbed to the surface, i.e., the multilayer only contained PAA and PDADMA within the bulk. Thus, it is clearly shown that polyelectrolyte bearing zwitterionic repeat units only do not form stable multilayers. By contrast, stable multilayers could be built with a copolymer comprising both zwitterion repeat units and a charged pH-responsive repeat units, such as acrylic acid, as seen in the thickness measurements in FIG. 10. FTIR revealed, in this case, the characteristic zwitterion peaks in poly(acrylic acid)-co-poly(3-[2-(acrylamido)-ethyldimethyl ammonio] propane sulfonate), PAA-co-PAEDAPS, copolymer, showed increasing quantities of zwitterion copolymer as the number of added layers increased, for a multilayer with the positive polyelectrolyte PAH. This clearly shows how the copolymer can be used in layer-by-layer buildup in contrast to the pure zwitterion polymer. The net negative charge on the zwitterion-bearing polyelectrolyte copolymer stabilizes the multilayer by providing ion pairing interaction points with oppositely charged groups on other polyelectrolyte molecules.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A method for causing a membrane to become permeable to a first chemical species, the method comprising:
    contacting the membrane with a solution comprising a second chemical species, wherein (1) the membrane comprises a polyelectrolyte complex film, the polyelectrolyte complex film comprising a positively-charged polyelectrolyte and a negatively-charged polyelectrolyte, (2) the second chemical species selectively interacts with the membrane, and (3) selective interaction of the second chemical species with the membrane causes the membrane to become permeable to the first chemical species, thereby causing the first chemical species to permeate the membrane.

2. The method of claim 1 wherein the selective interaction of the second chemical species with the membrane is measured by a distribution coefficient, K, wherein K is a ratio of a concentration of the second chemical species in the membrane to a concentration of the second chemical species in the solution, and the value of K at equilibrium is greater than 2.

3. The method of claim 2 wherein the value of K at equilibrium is greater than 10.

4. The method of claim 2 wherein the value of K at equilibrium is greater than 100.

5. The method of claim 1 wherein the polyelectrolyte complex film comprises multiple contact points for a polyvalent species comprising ion pairing groups and the second chemical species that interacts selectively with the polyelectrolyte complex film is the polyvalent species.

6. The method of claim 5 wherein the polyvalent species has a net charge greater than 2 or a net charge less than 2−.

7. The method of claim 5 wherein the polyvalent species is hexacyanocobaltate ion.

8. The method of claim 1 wherein the polyelectrolyte complex film comprises a polynucleotide and the second chemical species that interacts selectively with the polyelectrolyte complex film is a complementary polynucleotide sequence.

9. The method of claim 1 wherein the polyelectrolyte complex film comprises a polypeptide and the second chemical species that interacts selectively with the polyelectrolyte complex film is a complementary polypeptide.

10. The method of claim 1 wherein the polyelectrolyte complex film comprises an antibody and the second chemical species that interacts selectively with the polyelectrolyte complex film is a complementary antigen.

11. The method of claim 1 wherein the polyelectrolyte complex film comprises an antigen and the second chemical species that interacts selectively with the polyelectrolyte complex film is a complementary antibody.

12. The method of claim 1 wherein the polyelectrolyte complex film comprises an enzyme selected from the group consisting of metalloenzymes, metallothioneins, and calmodulin and the second chemical species that interacts selectively with the polyelectrolyte complex film is a metal ion for which the enzyme is selective.

13. The method of claim 1 wherein the negatively-charged polyelectrolyte comprises charged repeat units selected from the group consisting of styrenesulfonic acid, 2-acrylamido-2-methyl-1-propane sulfonic acid, sulfonated lignin, ethylenesulfonic acid, methacryloxyethylsulfonic acid, sulfonated ether ether ketone; and
    the positively-charged polyelectrolyte comprises charged repeat units selected from the group consisting of diallyldimethylammonium, vinylbenzyltrimethylammonium, ionenes, acryloxyethyltrimethyl ammonium chloride, methacryloxy (2-hydroxy)propyltrimethyl ammonium, N-methylvinylpyridinium, other N-alkylvinyl pyridiniums, N-aryl vinyl pyridinium, alkyl- or aryl imidazolium, crylic acids, methacrylic acid, carboxylic acids, pyridines, imidazoles, piperidines, and primary, secondary, or tertiary amines.

14. The method of claim 1 wherein the membrane forms a hollow capsule, the first chemical species is initially located inside the capsule, and selective interaction of the second chemical species with the membrane causes the hollow capsule to release the first chemical species.

15. The method of claim 1 wherein the membrane forms a hollow capsule, the first chemical species is initially located outside the capsule, and selective interaction of the second chemical species with the membrane causes the capsule to become loaded with the first chemical species.

16. The method of claim 1 wherein the negatively-charged polyelectrolyte comprises polynucleotide; and the positively-charged polyelectrolyte comprises charged repeat units selected from the group consisting of diallyldimethylammonium, vinylbenzyltrimethylammonium, ionenes, acryloxyethyltrimethyl ammonium chloride, methacryloxy (2-hydroxy)propyltrimethyl ammonium, N-methylvinylpyridinium, other N-alkylvinyl pyridiniums, N-aryl vinyl pyridinium, alkyl- or aryl imidazolium, crylic acids, methacrylic acid, carboxylic acids, pyridines, imidazoles, piperidines, and primary, secondary, or tertiary amines.

\* \* \* \* \*